US012751851B2

(12) United States Patent
Mali

(10) Patent No.: US 12,751,851 B2
(45) Date of Patent: Oct. 6, 2026

(54) ORTHOSIS FOR CLUBFOOT (CTEV) CORRECTION AND MAINTENANCE BASED ON PONSITI METHOD

(71) Applicant: JAIPUR CLUB FOOT PRIVATE LIMITED, Jaipur (IN)

(72) Inventor: Harlal Singh Mali, Jaipur (IN)

(73) Assignee: Jaipur Club Foot Private Limited, Jaipur (IN)

( * ) Notice: Subject to any disclaimer, the term of this patent is extended or adjusted under 35 U.S.C. 154(b) by 575 days.

(21) Appl. No.: 18/272,822

(22) PCT Filed: Dec. 29, 2021

(86) PCT No.: PCT/IN2021/051212
§ 371 (c)(1),
(2) Date: Jul. 18, 2023

(87) PCT Pub. No.: WO2022/157799
PCT Pub. Date: Jul. 28, 2022

(65) Prior Publication Data
US 2024/0082037 A1 Mar. 14, 2024

(30) Foreign Application Priority Data
Jan. 23, 2021 (IN) ............................ 202111003245

(51) Int. Cl.
*A61F 5/01* (2006.01)

(52) U.S. Cl.
CPC .... *A61F 5/0127* (2013.01); *A61F 2005/0137* (2013.01); *A61F 2005/0146* (2013.01); *A61F 2005/0179* (2013.01)

(58) Field of Classification Search
CPC ........ A61F 5/01; A61F 5/0102; A61F 5/0123; A61F 5/14; A61F 5/0119; A61F 5/0127;
(Continued)

(56) References Cited

FOREIGN PATENT DOCUMENTS

IN 201811028509 A * 8/2018 ........... A61F 5/0127

OTHER PUBLICATIONS

Kanwaljit S. Kas, Development of an orthosis for simultaneous three-dimensional correction of clubfoot deformity, Clinical Biomechanics, 2 018, vol. 51, 67-75 DOI: 10.1016/j.clinbiomech.2017.12.002.

(Continued)

*Primary Examiner* — Daniel A Miller
(74) *Attorney, Agent, or Firm* — Bay State IP, LLC

(57) ABSTRACT

This invention relates to Orthosis for clubfoot (CTEV) Correction and Maintenance based on Ponsiti Method.
CTEV (clubfoot) is a congenital deformity prevalent to one in 800 children born. Very few attempts have been made to correct and maintain CTEV deformity by unilateral orthosis, which are associated with drawbacks and hence not effective.
The Orthosis comprising metatarsal top (1), metatarsal bottom (2) and pitch and yaw link (3) connected together by an actuator A1 (13) with the pitch and yaw link (3) placed between the metatarsal top and metatarsal bottom, wherein the metatarsal top (1) and metatarsal bottom (2) are provided with strap slots (1*b*, 2*b*) for holding baby foot;
The pitch and yaw link (3) is connected to forefoot roll link (4). The forefoot roll link (4) is connected to upper and top bases of hind foot assembly (5, 6) to execute the rolling motion of the forefoot.

15 Claims, 22 Drawing Sheets

(58) Field of Classification Search
CPC ........ A61F 5/0193; A61F 5/042; A61F 5/013; A61F 5/0125; A61F 2005/0132; A61F 2005/0141; A61F 2005/0144; A61F 2005/0151; A61F 2005/0155; A61F 2005/0137; A61F 2005/0146; A61F 2005/0179; A61F 2005/0165; A61F 2005/0134; A61F 2005/0167; A61F 2005/016; A61F 2005/0139
USPC ............................................................ 602/16
See application file for complete search history.

(56) References Cited

OTHER PUBLICATIONS

International Search Report, Indian Patent Office, Mar. 4, 2022.

* cited by examiner

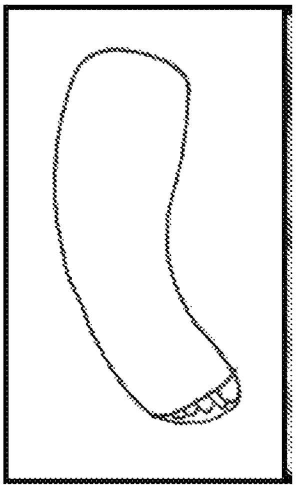
(a)
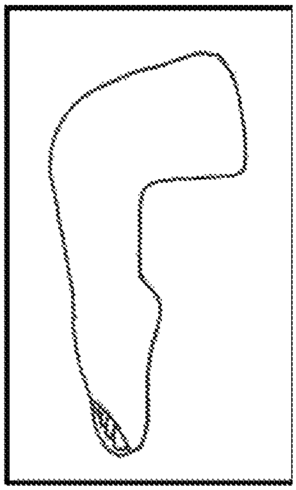
(b)
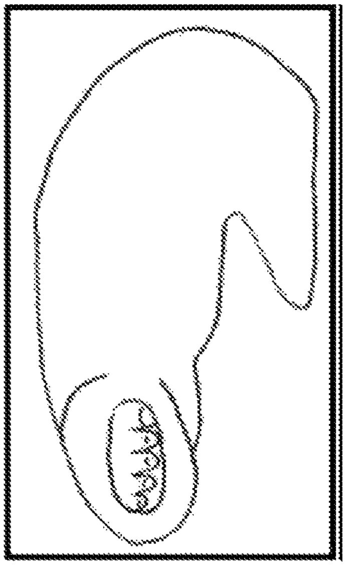
(c)
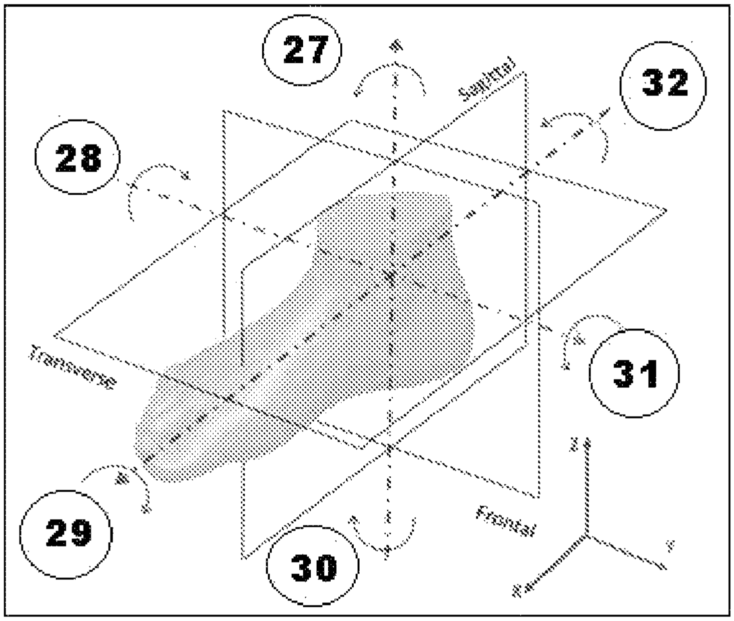
(d)
Fig: 2

2nd

3rd

4th

ORTHOSIS FOR CLUBFOOT (CTEV) CORRECTION AND MAINTENANCE BASED ON PONSITI METHOD

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/IN2021/051212 filed on Dec. 29, 2021, and in which in turn claims priority under 35 USC 119 to Indian Patent Application No. 202111003245 filed on Jan. 23, 2021.

FIELD OF INVENTION

This invention relates to an orthosis for clubfoot (CTEV) correction and maintenance based on a manipulative casting method otherwise known as the Ponseti® Method.

The orthosis involves eight motions, out of which first six are corrective motions, three at forefoot level and three at hind foot level and out of the other two motions, one caters to the growth of leg of the patient and another one knee movement of the patient.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Clubfoot, mainly CTEV (Congenital Talipes Equino Varus), is a complex three-dimensional deformity, challenging physicians from ancient times. Among one thousand babies born, 1-6 suffer from clubfoot deformity. In India alone, around 35,000 need treatment for clubfoot annually. 80% of the cases of clubfoot are from lower and middle income countries (LMICs). Among the children affected by clubfoot, 50% of cases are of bilateral deformity i.e. both feet are affected.

Current CTEV Treatment: A Manipulative Casting Method (The Ponseti®) Method)

The most popular, widely accepted and successful method for clubfoot treatment was developed by Dr Ponseti and his method is known as the Ponseti® Method. In this method, the deformity is corrected by a series of manipulations through castings by the clinicians followed by maintenance using a bilateral FAB (Foot Abduction Brace). Manipulations are based on the understanding of the biomechanics of the foot. During correction, with the lateral aspect of the talus head as a fulcrum, the foot follows its natural path in pronation as a closed kinematic chain comprising a forefoot and a hindfoot, as shown in FIG. 1. This technique involves the simultaneous correction of all deformities except an equinus deformity. After the manipulations are made by the clinician (FIG. 1), the cast is applied to hold the CTEV affected foot in the corrected position.

The first manipulation is to correct the cavus deformity. For correcting this the following steps are carried out as shown in FIG. 2:

i. Stabilizing the talus by placing the thumb over the lateral part of the head of the talus.
ii. Elevating the first ray and achieving a homogeny supination of the forefoot in line with the midfoot, then abducting the foot gently.
iii. Holding the corrected position while an assistant applies padding and plaster. Changing hand positions and moulding well at the heel, malleoli, and the sole of the foot.

In small babies, correction of the cavus usually occurs with the first cast, whereas, a severe cavus in a stiff foot (older babies) will need 2 or 3 cast changes for correction.

After achieving a normal arch through cavus correction, correction of midfoot inversion and heel varus is carried out through successive casts as shown in FIG. 3.

In a "younger child" (i.e. who has not walked before treatment) the target abduction range is 50°-60° with the heel in the neutral position. In an "older child" (i.e. who has already walked before treatment), the target abduction range is 30°-50° with the heel in the neutral position.

The procedure is as follows:

i. Stabilizing the talus by placing the thumb over the lateral part of the head of the talus.
ii. Holding the foot in abduction with the appropriate degree of supination while applying the cast. Supination decreases with the increase of abduction. At about 50° abduction, the foot no longer needs to be maintained in the supine position, but the foot is never to be held in a prone position.
iii. The correction of the calcaneus is achieved because of coupling. Plaster should be done as often possible to get enough abduction.
iv. The corrected position is held by the clinician, while an assistant applies padding and plaster. Moulding is done by changing hand positions.

When the desired abduction is achieved, the next step is the correction of rigid equinus in the ankle. This requires an Achilles tendon tenotomy (a minor surgical procedure) in most cases. After that, plaster is applied for 3 weeks to maintain the foot in the corrected position through the following procedure:

i. Stabilizing the talus by placing the thumb over the lateral part of the head of the talus.
ii. Moving the foot in maximal possible abduction without any pronation and then into dorsiflexion in the ankle with the lower hand. By abducting, the navicular should now fully cover the head of the talus, so that the thumb will lose the ability to palpate the lateral head of the talus. The thumb, which stabilized the talus in the beginning, is removed and then moves the foot into dorsiflexion. To achieve a better dorsiflexion, the heel should be pulled down, and gentle pressure should be applied under the entire sole to put the foot into dorsiflexion. Applying mere force or pressure in the forefoot area trying to achieve more dorsiflexion is never to be done, as it can cause a rocker bottom deformity. After maximal abduction and dorsiflexion has been achieved, moving the lower hand to the toes of the child is advisable before casting.
iii. The clinician should hold the corrected position while an assistant applies padding and plaster. Moulding is done effectively at the heel, malleoli and sole of the foot by changing hand positions.

After the cast is removed, the foot may appear overcorrected, but "hyperabduction" of 70° in babies is a helpful measure to prevent a recurrence.

After the correction is achieved, the maintenance phase starts. In the maintenance phase as shown in FIG. 3(*b*), a foot abduction orthosis/brace (FAO/FAB) is recommended for 23 hours per day initially up to 3 months. In the case of unilateral deformity, the corrected foot is placed at 70 degrees and the unaffected foot is placed at a 40-degree abduction whereas in bilateral cases both the feet are in 70-degree abduction. After 3 months, it is recommended to use boots in daytime and FABs in night time for up to 3 years for maintenance of the correction achieved through castings.

Limitation of the Manipulative Casting Method (the Ponseti® Method):

Various studies establish that the Ponseti® Method (the manipulative casting method) has been a gold standard in clubfoot treatment for 50 years. However, this method suffers from issues like multiple visits to clinicians, excessive travel requirements for patients, extended clinician involvement, high dependency on the skill levels of the clinicians, skin ulcers on patients and minimal contemporary technological intervention in treatment etc., which leads to non-start/discontinuation of the treatment, leading to lifelong permanent deformity in the patient, requiring a complex surgical procedure. Almost 50% of the children with clubfoot deformity are left untreated due to these challenges. The bilateral FAB (foot abduction brace), even if the deformity is unilateral, is a social stigma to the patient and family and such perceptions have led to impairing the patient's natural growth.

Prior Art of the Invention:

Few successful attempts have been made to correct and maintain CTEV deformity by the unilateral orthosis. Faraj et al [1] tested an orthosis called "Clubax" for clubfoot treatment. The study was carried out from April 1996 to September 1998. The corrective orthosis was applied on 14 patients (21 feet) with an average period of 3 months (varying between 2-4 months). The follow-up period was from 5-32 months with an average of 15 months. Lugo et al [2] developed another corrective orthosis. The corrective orthosis design allowed 4 degrees of freedom (DOF). The orthosis was tested on a unilateral clubfoot in a single patient for 8 months. Kanwaljit et al [3] developed a 3 DOF based orthosis and tested it on 5 patients for one week. Mohamaddan et al [4], developed an adjustable foot corrective device for clubfoot treatment. Vishnu et al [5], attempted designing and developing an orthosis for clubfoot correction in infants using an additive manufacturing approach.

However, none of the above attempts succeeded in treating CTEV mainly because they did not follow the foot biomechanics as proposed by Dr. Ponseti. In low and middle income countries no further studies are available in literature for the utility of these orthoses, where such devices are needed the most. In this regard Mali H S, et al. [6] attempted developing a remedial orthosis for CTEV (clubfoot) through five corrective motions. However, further development is required, especially development that is in line with Ponseti's understanding of foot biomechanics.

Based on the foot biomechanics understood by Dr. Ponseti there is a need for an orthosis using state-of-the-art technological intervention to overcome the above problems and enhance the CTEV treatment experience at all stakeholder levels, i.e. patients, patient parents, clinicians, and society. Hence, the present invention has been introduced, that serves the purpose effectively.

OBJECTS OF THE INVENTION

An object of the invention is to provide an orthosis for clubfoot (CTEV) correction and maintenance based on the Ponseti® Method (the manipulative casting method), which obviates shortcomings of the prior art(s).

Still another object of the invention is to provide an orthosis for clubfoot (CTEV) correction and maintenance based on the Ponseti® Method (the manipulative casting method), which is simple in construction.

Yet another object of the invention is to provide an orthosis for clubfoot (CTEV) correction and maintenance based on the Ponseti® Method (the manipulative casting method), which effectively serves the purpose.

Yet another object of the invention is to provide an orthosis for clubfoot (CTEV) correction and maintenance based on the Ponseti® Method (the manipulative casting method), which incorporates contemporary and futuristic technologies.

These and other objects and advantages of the present invention will be apparent to those skilled in the art after a consideration of the following detailed description taken in conjunction with the accompanying drawings in which a preferred form of the present invention is illustrated.

SUMMARY OF THE INVENTION

One or more drawbacks of conventional systems and process are overcome, and additional advantages are provided through the apparatus/composition and a method as claimed in the present disclosure. Additional features and advantages are realized through the technicalities of the present disclosure. Other embodiments and aspects of the disclosure are described in detail herein and are considered to be part of the claimed disclosure.

According to the invention, there is provided an orthosis for clubfoot (CTEV) correction and maintenance based on the Ponseti® Method (the manipulative casting method) comprising a metatarsal top link (1), a metatarsal bottom link (2) and a pitch and yaw link (3) connected together by an actuator A1 (13) with the pitch and yaw link (3) placed between the metatarsal top link (1) and the metatarsal bottom link (2), wherein the metatarsal top link (1) and the metatarsal bottom link (2) are each provided with a pair of strap slots (1*b*, 2*b*) allowing a passage of a forefoot strap through the pair of strap slots (1*b*, 2*b*) for holding a baby foot;

- the pitch and yaw link (3) is connected to a forefoot roll link (4);
- the forefoot roll link (4) is connected to a hind foot assembly comprising a hind foot bottom base (5) and a hind foot top base (6) configured to execute a rolling motion of a forefoot;
- a yaw guide base (7) has a rotating joint with the hind foot top base (6) and is configured to provide a rolling motion of a hind foot;
- the yaw guide base (7) slides on a hind foot yaw link (8) and is configured to provide a yawing motion of the hind foot;
- the hindfoot yaw link (8) is suspended on a pair of calf support links (9) on a first side and a second side of the hind foot yaw link (8);
- a calf muscle support (10) attached to the pair of calf support links (9) and configured to support the calf muscle.

The metatarsal top link (1) is superimposed on the metatarsal bottom link (2), each of which is provided with one of the pair of strap slots (1*b* and 2*b*) and are configured to hold the baby foot, wherein the metatarsal top link (1) and the metatarsal bottom link (2) are coupled with the pitch and yaw link (3) and are configured to support a plurality of metatarsals and to perform a yawing motion of the forefoot buoyed by the actuator A1 (13) through a first hole (3*a*), in which the actuator A1 (13) passes through a plurality of holes including the first hole (1a, 2a, 3a).

The pitch and yaw link (3) is held in place and connected to the forefoot roll link (4) by an actuator A2 (14) passing through a keyhole on the pitch and yaw link (3) and a keyhole on the forefoot roll link (4).

The forefoot roll link (4) comprises a rotating joint with the pitch and yaw link (3) configured to cause a pitching motion of the forefoot through an actuator A2 (14), in which the hind foot top base (6) is secured with the hind foot bottom base (5) and the forefoot roll link (4) is joined with the hind foot bottom base (5) and the hind foot top base (6) and is configured to provide the rolling motion of the forefoot using an actuator A3 (15), wherein the hind foot top base (6), the hindfoot bottom base (5) and the forefoot roll link (4) are connected to each other via said actuator A3 (15).

The hind foot assembly encompasses the hind foot bottom base (5), the hind foot top base (6) and the yaw guide base (7), in which the hind foot top base (6) is configured to support a talus.

The yaw guide base (7) has a rotating joint with the hind foot top base (6) to provide the rolling motion of the hind foot through an actuator A4 (16).

The yaw guide base (7) slides on a hind foot yaw link (8) to provide the yawing of the hind foot through the actuator A4 (16).

The hind foot yaw link (8) is suspended on the pair of calf support links (9) on the first side and the second side of the hind foot yaw link (8) by an actuator A5 (17) through a hole (8a) on the hind foot yaw link (8) and a hole (9d) on at least one of the pair of calf support links (9) and is configured to cause a pitching motion of the hind foot.

The calf muscle support (10) is fixed to the pair of calf support links (9) using a fastener including a bolt (18) passing through a plurality of holes (9a & 10a), and wherein the pair of calf support links (9) comprise a multitude of holes (9b) at different levels/heights to be locked with a slider link (11) using a slider bolt (19), in which the slider link (11) has a pair of embedded nuts and bolt holes (11a, 11b) and each of the pair of calf support links (9) has a plurality of slots (9e, 9f) to draw a plurality of calf straps therethrough that are configured to tie around a leg.

A pair of slider links (11) are attached to the pair of calf support links (9), the pair of calf support links (9) having a plurality of holes (9b), which allows the pair of slider links (11) to have a linear motion inside the pair of calf support links (9), wherein the linear motion is configured to compensate for a growth of a leg during a treatment.

The calf muscle support (10) comprises a protrusion on a right side of the calf muscle support (10) and a protrusion on a left side of the calf muscle support (10), wherein each protrusion comprises a plurality of holes (10a) therein.

The orthosis includes a pair of thigh links (12) configured to attach and ground the orthosis with a patient thigh using a plurality of thigh straps passing through a slot (12a), wherein the pair of thigh links (12) are connected with a pair of slider links (11) through a rotating joint, for which a fastener including a bolt (18) passes between two holes (11a and 12b).

The thigh link (12) has a hole (12b) at which one side of a slider link (11) is attached to using a slider bolt (19), wherein the thigh link (12) further has a pair of slots (12a) for a plurality of thigh straps that are configured to be secured around a thigh and support the thigh even when a knee is bent.

The orthosis involves eight motions, the eight motions comprising the rolling motion of the forefoot, a yawing motion of the forefoot, a pitching motion of the forefoot, the rolling motion of the hind foot, the yawing motion of the hind foot, a pitching motion of the hind foot, a motion configured to cater to a leg growth of a patient, and a motion configured to cater to knee movement of the patient.

The orthosis relies on indexing a rotary motion to lock and unlock the orthosis using a plurality of splines created on an outer body (24), an inner slider (21) and an outer cap (20), in which the inner slider (21) in an initial position rests midway between the outer cap (20) and the outer body (24) making the plurality of splines interlock the outer cap (20) and the outer body (24), wherein upon activation of an electromagnet (22), a permanent magnet (25) attached permanently to the inner slider (21) is repelled towards the outer cap (20) allowing for a rotation of the outer cap (20) facilitated by a motor (23), wherein once a predetermined amount of rotation is achieved, the electromagnet (22) is deactivated and a spring (26), attached to both the outer cap (20) and the inner slider (21) restores the inner slider (21) to the initial position, locking the orthosis in place until a manipulation is required.

The lock and unlock provisions along with dial gauges to all the six corrective motion mechanisms permit the clinicians to manipulate and hold various parts of the foot for successive corrections.

During manual operation, a hex key is inserted into a cavity in the outer cap (20) that pushes onto the inner slider (21) to cause the inner slider (21) to slide away from the outer cap (20) and then be restored to an original position as the spring (26) contracts to bring the inner slider (21) back to the original position and lock the inner slider (21) in place when the hex key is removed.

The corrective orthosis has a provision of a closed loop actuator, including the actuator A1 (13), along with a plurality of sensors for step motion as well as locking/unlocking mechanism.

The closed loop actuator along with the plurality of sensors help in data recording by a controller cum data acquisition system and hence deformity measurement and database creation before, during, and after the treatment of the patient can be automated.

Various objects, features, aspects, and advantages of the inventive subject matter will become more apparent from the following detailed description of preferred embodiments, along with the accompanying drawing figures in which like numerals represent like components.

It is to be understood that the aspects and embodiments of the disclosure described above may be used in any combination with each other. Several of the aspects and embodiments may be combined to form a further embodiment of the disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein, wherein:

FIG. 1 shows: The manipulative casting method (the Ponseti® Method) technique.

FIG. 2 collectively shows: The manipulative casting method (the Ponseti® Method) for clubfoot 1$^{st}$ cast in different views in reference planes.

FIG. 2(*a*) shows: A frontal view of clubfoot 1$^{st}$ cast.

FIG. 2(*b*) shows: A medial (sagittal) view of clubfoot 1$^{st}$ cast.

FIG. 2(*c*) shows: A caudal (anterior) view of clubfoot 1$^{st}$ cast.

FIG. 2(*d*) shows: Reference planes of clubfoot 1$^{st}$ cast indicating the following:

Abduction (Yawing-in)—27,
Dorsiflexion (Pitching-up)—28,
Eversion (Rolling-CW from-Front)—29,
Abduction (Yawing-out)—30,
Plantarflexion (Pitching-down)—31,
Inversion (Rolling-CCW from Front)—32

FIG. 3(*a*) shows: 2$^{nd}$ to 4$^{th}$ casts in the manipulative casting method (the Ponseti® Method) for clubfoot adduction and varus correction.

FIG. 3(*b*) shows: A foot abduction orthosis/brace (FAO/FAB) used during a maintenance phase of the manipulative casting method (the Ponseti®) Method).

FIG. 4 collectively shows: Parts of the manipulative casting method (the Ponseti® Method) based on an orthosis for CTEV (clubfoot) correction and maintenance according to the present invention.

FIG. 4(*a*) shows: A side view of the CTEV orthosis.

FIG. 4(*b*) shows: A rear view of the CTEV orthosis.

FIG. 4(*c*) shows: A cross-sectional top view (plane C-C from FIG. 4(*a*)) of the CTEV orthosis.

FIG. 4(*d*) shows: A sectional front view (plane D-D from FIG. 4(*a*)) of an actuator A2 (14) between a pitch and yaw link (3) and a forefoot roll link (4).

FIG. 4(*e*) shows: A top view of a metatarsal top link (1) with a first hole (1*a*) and a cut section (1*b*).

FIG. 4(*f*) shows: A top view of a metatarsal bottom link (2) with a dial gauge, a hole (2*a*) and a cut section (2*b*).

FIG. 4(*g*) shows: A top view and side view of the pitch and yaw link (3) with holes (3*a* and 3*b*).

FIG. 4(*h*) shows: A side and back view of a forefront roll link (4) with holes (4*a* and 4*b*).

FIG. 4(*i*) shows: A front view of a hindfoot bottom base (5) with a cut section (5*a*).

FIG. 4(*j*) shows: A front and side view of a hindfoot top base (6) with a hole (6*a*) and cut sections (6*b* and 6*c*).

FIG. 4(*k*) shows: A back and side cross-sectional view of a yaw guide base (7) with holes (7*a* and 7*b*).

FIG. 4(*l*) shows: A side view of a hindfoot yaw link (8) with a hole (8*a*).

FIG. 4(*m*) shows: A side and cross-sectional view of a calf support link (9) with holes (9*a*, 9*b*, 9*c*, 9*d*) and cut sections (9*e* and 9*f*).

FIG. 4(*n*) shows: A front view of a calf muscle support (10) with a hole (10*a*).

FIG. 4(*o*) shows: A side view of a slider link (11) with a hole (11*a*) and a cut section (11*b*).

FIG. 4(*p*) shows: A side view of a thigh link (12) with a cut section (12*a*) and a hole (12*b*).

FIG. 5 collectively shows: The orthosis supporting the forefoot motions in accordance with the present invention.

FIG. 5(*a*) shows: The rolling motion of the forefoot (inversion/eversion).

FIG. 5(*b*) shows: The yawing motion of the forefoot (abduction/adduction).

FIG. 5(*c*) shows: The pitching motion of the forefoot (dorsiflexion/plantarflexion).

FIG. 6 collectively shows: The orthosis supporting the hindfoot motions.

FIG. 6(*b*) shows: The yawing motion of the hind foot (abduction/adduction).

FIG. 6(*c*) shows: The pitching motion of the hind foot (dorsiflexion/plantarflexion).

FIG. 8(*a*) shows: A bottom view of a forefoot yawing motion with a dial gauge.

FIG. 8(*b*) shows: The mechanism for step motion actuation in the orthosis for corrective motions.

Figure 10A:
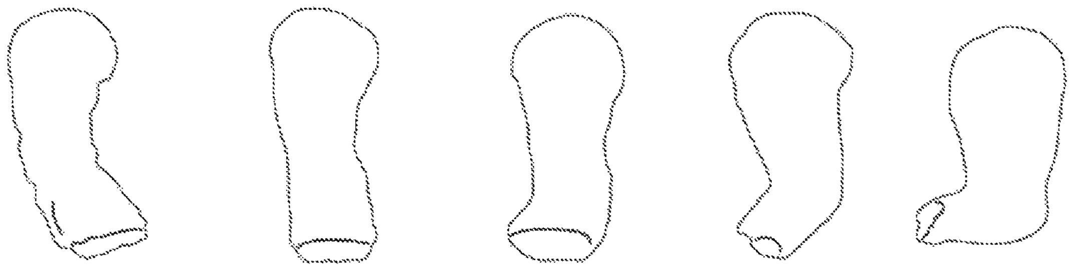
Figure 10B:
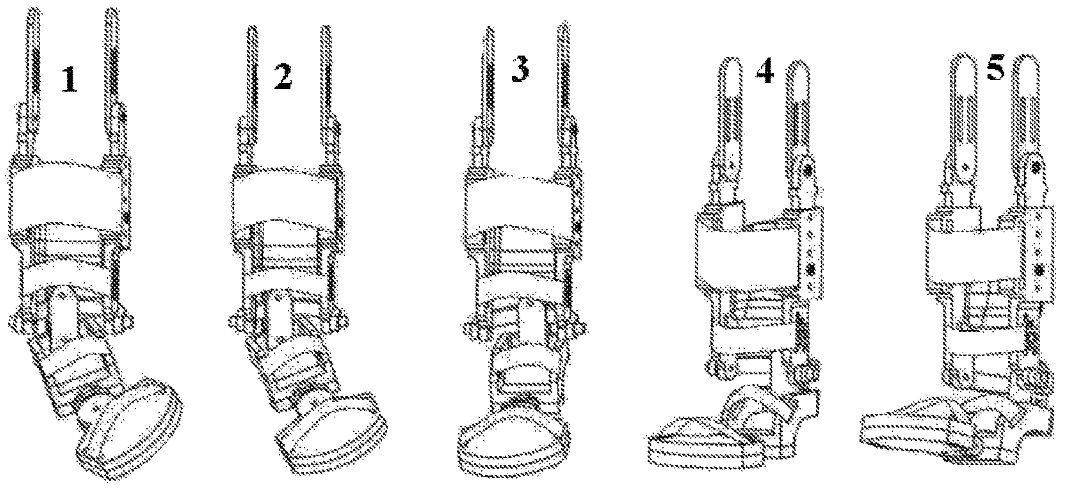
Figure 10C:
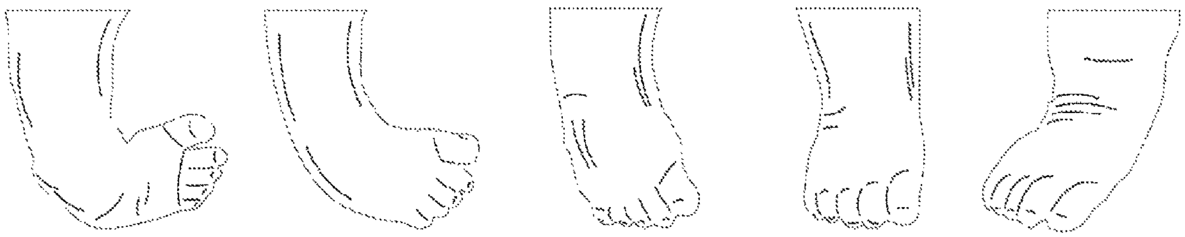

FIG. 10 collectively shows: The corrective orthosis motions being performed similar to casting in the manipulative casting method (the Ponseti®) Method).

FIG. 10(*a*) shows: The cast for foot correction in succession as per the manipulative casting method (the Ponseti® Method).

FIG. 10(*b*) shows: The foot correction position of corrective orthosis in succession similar to casts in the manipulative casting method (the Ponseti® Method).

FIG. 10(*c*) shows: The foot inside the cast as well as the orthosis in successive correction.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION WITH REFERENCE TO THE ACCOMPANYING DRAWINGS OF PREFERRED EMBODIMENTS OF THE INVENTION

While the embodiments of the disclosure are subject to various modifications and alternative forms, specific embodiments thereof have been shown by way of example in the figures and will be described below. It should be understood, however, that it is not intended to limit the disclosure to the particular forms disclosed, but on the contrary, the disclosure is to cover all modifications, equivalents, and alternatives falling within the scope of the disclosure.

The present invention is directed to an invention pertinent to an orthosis for clubfoot (CTEV) correction and maintenance based on a manipulative casting method otherwise known as the Ponseti® Method.

The developed orthosis is based on Dr. Ponseti's understanding of foot biomechanics and the Ponseti® Method (the manipulative casting method) of CTEV treatment. It allows the calcaneus to be free from any reaction force and a provision to hold the talus head as a fulcrum during manipulations. This allows the hind foot to follow the forefoot in a natural manner similar to the Ponseti® Method. The developed orthosis (FIG. 4) of the present invention incorporates a total of eight motions, out of which six are corrective motions (e.g., a rolling motion of the forefoot, a yawing motion of the forefoot, a pitching motion of the forefoot, a rolling motion of the hind foot, a yawing motion of the hind foot, and a pitching motion of the hind foot), one motion caters to leg growth of a patient, and another motion caters to knee movement of the patient.

The lock and unlock provisions along with dial gauges to all the six corrective motion mechanisms permit the clinicians to manipulate and hold various parts of the foot for successive corrections. The closed loop actuator along with sensors help in data recording by the controller cum data acquisition system and hence deformity measurement and database creation before, during and after the treatment of the patient can be automated.

The product of the proposed application is an externally applied brace (orthosis) to modify the structural and functional characteristics of defective feet. It aims at correcting CTEV based on the Ponseti® Method (the manipulative casting method). The orthosis for CTEV (clubfoot) correction and maintenance implementing the Ponseti® Method (the manipulative casting method) comprises rigid links/parts (FIG. 4) to form various motions.

Now, reference may be made to the accompanying FIG. 4. The orthosis includes a metatarsal top link (1) superimposed on a metatarsal bottom link (2), each of which is provided with a pair of strap slots (1*b* and 2*b*) respectively so as to hold the foot as shown in FIGS. 4(*e*) and (*f*). There is a provision of a pitch and yaw link (3) having a rotating joint with the metatarsal top link (1) and the metatarsal bottom link (2) to allow a yawing motion of the forefoot using an actuator A1 (13).

An 'actuator' here is an assembly of a dial gauge for a specified motion and its locking/unlocking mechanism.

The metatarsal top link (1) and the metatarsal bottom link (2) are provided with the pair of strap slots (1*b*, 2*b*) allowing a passage of a forefoot strap through the pair of strap slots (1*b*, 2*b*) for holding a baby foot steadily after manipulations by means of the forefoot strap. The metatarsal top link (1) and metatarsal bottom link (2) have keyholes (1*a*, 2*a*) for the actuator A1 (13) to pass through at the center of a circular mating surface. The metatarsal top link (1) and the metatarsal bottom link (2) are coupled with the pitch and yaw link (3) to support the metatarsals to perform the forefoot yawing motion buoyed by the actuator A1 (13) through the hole (3*a*). Thus, the metatarsal top link (1), the metatarsal bottom link (2), and the pitch and yaw link (3) are connected together by the actuator A1 (13) with the pitch and yaw link (3) placed between the metatarsal top link (1) and the metatarsal bottom link (2). The actuator A1 (13) passes through the holes (1*a*, 2*a*, 3*a*) as described.

The pitch and yaw link (3) is held in place and connected to the forefoot roll link (4) by an actuator A2 (14) passing through a keyhole on the pitch and yaw link (3) and a keyhole on the forefoot roll link (4) as indicated in FIGS. 4(*g*) and (*h*). The forefoot roll link (4) is further crammed in/connected to a hind foot assembly comprising a hind foot bottom base (5) and a hind foot top base (6) to execute the rolling motion of the forefoot.

The forefoot roll link (4) includes a rotating joint with the pitch and yaw link (3) configured to cause a pitching motion of the forefoot through the actuator A2 (14). The hind foot top base (6) is fixed with the hindfoot bottom base (5) and the forefoot roll link (4) at a cylindrical joint to provide a rolling motion of the forefoot using an actuator A3 (15). Here, the hind foot top base (6), the hindfoot bottom base (5) and the forefoot roll link (4) are connected to each other via said actuator A3 (15).

The hind foot assembly encompasses the hind foot bottom base (5), the hind foot top base (6) and a yaw guide base (7). The hind foot top base (6) is principally made to support the talus. It positions the heel and entails strap slots (6*c*). There is a substantially cylindrical cavity (5*a*, 6*b*) as in FIGS. 4(*i*) and (*j*) flanked by the hind foot bottom base (5) and the hind foot top base (6) which shelter the forefoot roll link (4). According to the present invention, the forefoot rolling motion is controlled by the actuator A3 (15) which locks the forefoot roll link (4) and thus, provides a clean and intricate structure, and effective functionality to the orthosis of present invention for the particular motion.

The yaw guide base (7) slides on a hind foot yaw link (8) to provide a yawing motion of the hindfoot through an actuator A4 (16). The yaw guide base (7) has a rotating joint with the hind foot top base (6) to provide a rolling motion of the hind foot through the actuator A4 (16).

The yaw guide base (7) has two keyholes (7*a*), the lower one of which grips the hind foot top base (6) and directs the rolling motion of the hind foot using the actuator A4 (16); the upper hole (7*a*) clasps the hindfoot yaw link (8) through the actuator A4 (16). The actuator (A4 (16)) is responsible to uphold the yawing motion of the hind foot and its locking based on the sliding of the yaw guide base (7) on the hind foot yaw link (8) through the actuator A4 (16).

The pair of calf support links (9) as illustrated in FIG. 4(*m*) are attached to the hind foot yaw link (8) through a rotating joint through holes (9*d*). This joint facilitates the pitching motion of the hind foot using an actuator A5 (17). The slots (9*e* & 9*f*) are provided for straps to hold a leg of a patient.

The hind foot yaw link (8) is suspended on the pair of calf support links (9) on a first side and a second side of the hind foot yaw link (8) by actuator A5 (17) through holes on both the links (8*a*, 9*d*) respectively. This accomplishes the hindfoot pitching motion of the hind foot.

A calf muscle support (10) is provided to support a calf muscle of the patient and is fixed to the pair of calf support links (9) using a fastener including a (8) passing through holes (9*a* & 10*a*).

Each of the pair of calf support links (9) is a comparatively complex part with a provision of intermittent support for different leg lengths. This is achieved by making a multitude of holes (9*b*) on the calf support link (9) at different levels/heights to be locked with the slider link (11) using a slider bolt (19). The slider link (11) has a pair of embedded nuts and bolt holes (11*a*, 11*b*) for the same. The calf support link also has a plurality of slots (9*e*, 9*f*) to draw a plurality of calf straps therethrough to tie around the leg.

A pair of slider links (11) are attached to a hole of the multitude of holes (9*b*) of each of the pair of calf support links (9) using a slider bolt (19). Each of the pair of calf support links (9) have a multitude of holes (9*b*), which allows the pair of slider links (11) to have a linear motion inside the pair of calf support links (9) to compensate for the growth of the leg during the treatment.

The calf muscle support (10) is designed to support the calf muscle. It has a protrusion on a right side and a protrusion on a left side, wherein each protrusion includes a plurality of holes (10*a*) therein. As seen in the sectional view (E1-E1), there is an alternative pair of fasteners [nuts and bolt] holes (9*c*) on one side of the calf support link (9). These holes (9*c*) hold up the calf muscle support (10) in position using manifold bolts (18) passing through the plurality of holes (10*a*) in protruded parts of the calf muscle support (10).

The orthosis also includes a pair of thigh links (12) for attaching and grounding of the orthosis with the patient thigh using a plurality of thigh straps passing through a slot (12*a*) as shown in FIG. 4(*p*). The pair of thigh links (12) replicate the above-knee part of the cast. These pair of thigh links (12) are connected with the pair of slider links (11) through a rotating joint using a bolt (18) that passes between two holes (11*a* and 12*b*).

Each of the pair of thigh links (12) has a minimal structure with a hole (12*b*) to attach the slider link (11) on one side using a slider bolt (19). Its function is to support the thigh even when the knees are bent. This link has a pair of slots (12*a*) for the plurality of thigh straps to be secured around the thigh.

Orthosis motions: The orthosis is capable to have motions required as per the Ponseti® Method (the manipulative casting method). The six motions at foot level are sufficient to cater the manipulations required as per the Ponseti® Method (the manipulative casting method). These motions occur in a minimum step size of 5 degrees as per requirement of the clinician.

Figure 5A:
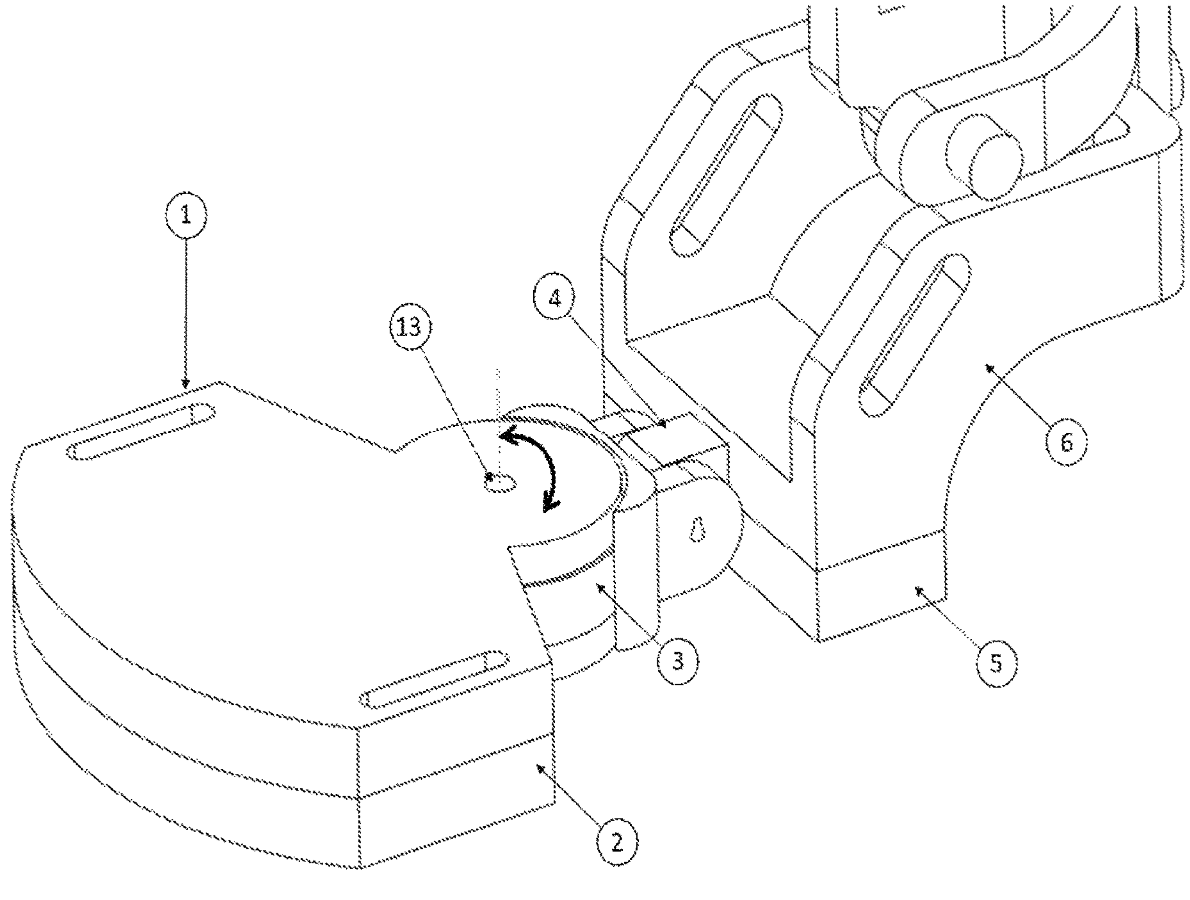
Figure 5B:
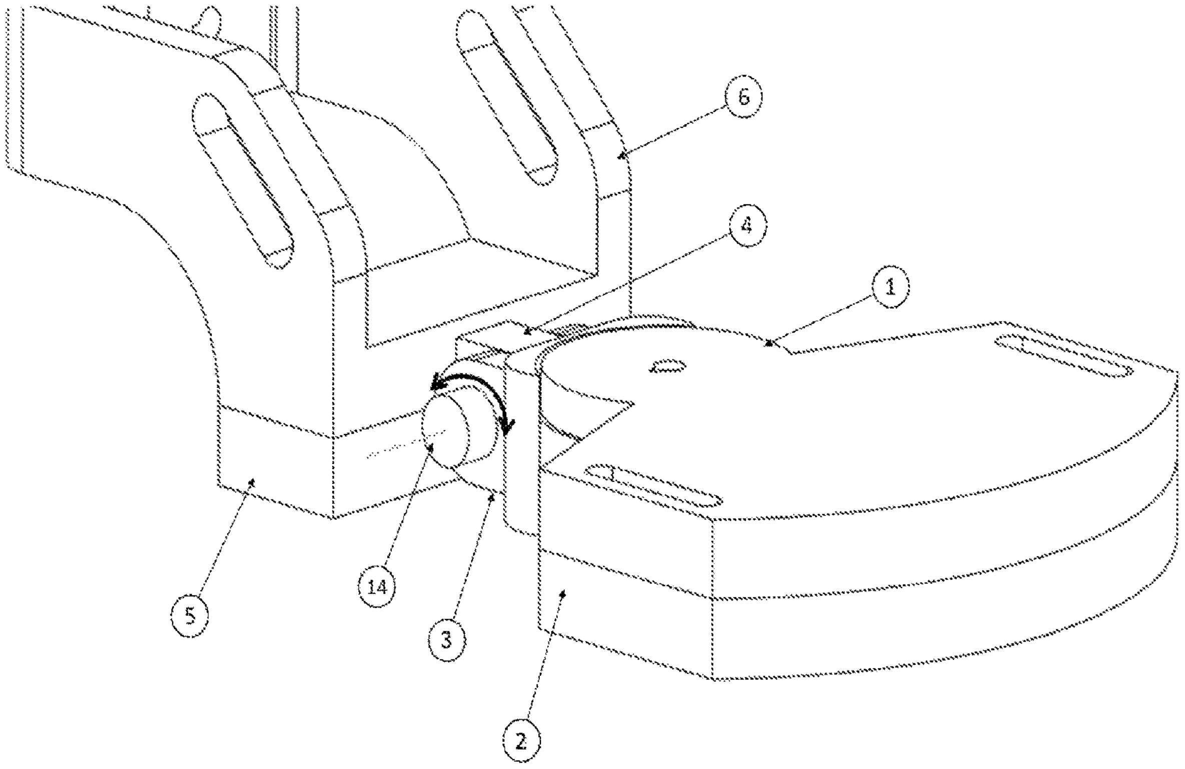
Figure 5C:
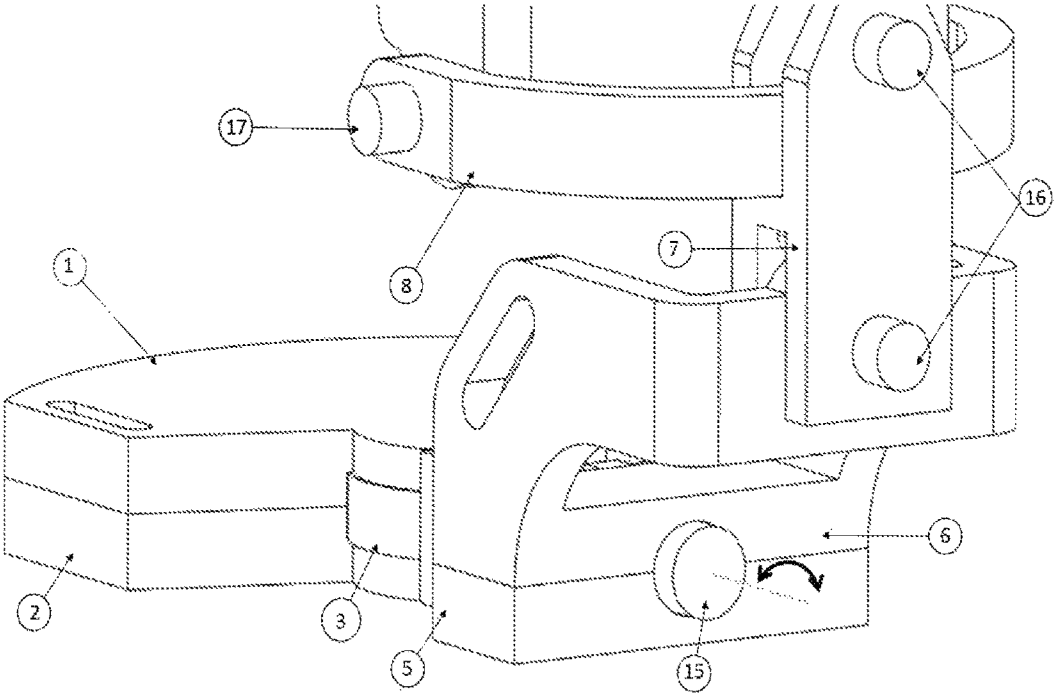

The abduction, eversion and dorsiflexion of the forefoot are handled by respective three motions in orthosis at forefoot level, as shown in FIG. 5. For the yawing motion of the forefoot, the actuator A1 (13) actuates and provides 70 degrees of adduction and abduction, as shown in FIG. 5(*a*). The pitching motion of the forefoot occurs with the actuation of the actuator A2 (14) with a range of 70-degree plantarflexion and 20-degree dorsiflexion, as indicated in FIG. 5(*b*). The rolling motion of the forefoot is handled by the actuator A3 (15) actuation, with a range of 70-degree inversion and 20-degree eversion, as shown in FIG. 5(*c*). All the motions are with reference to FIG. 2(*d*).

Figure 6A:
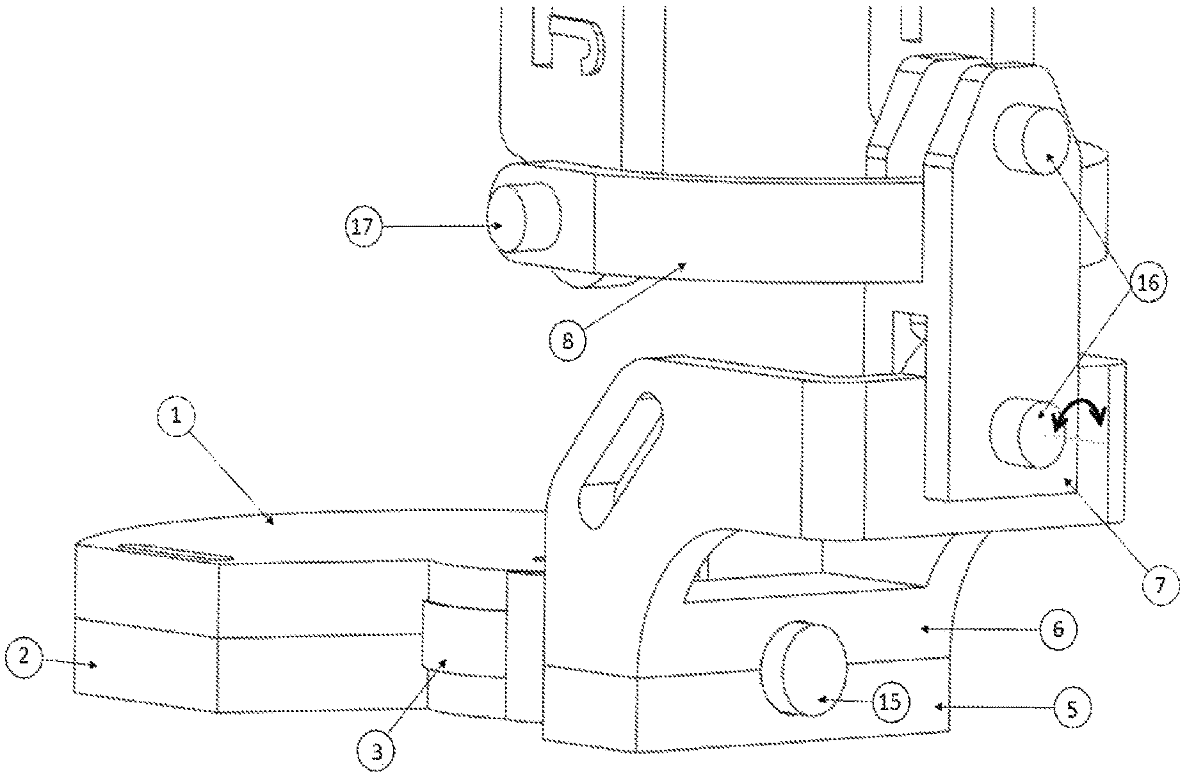
FIG. 6(*a*) shows: The rolling motion of the hind foot (inversion/eversion).
Figure 6B:
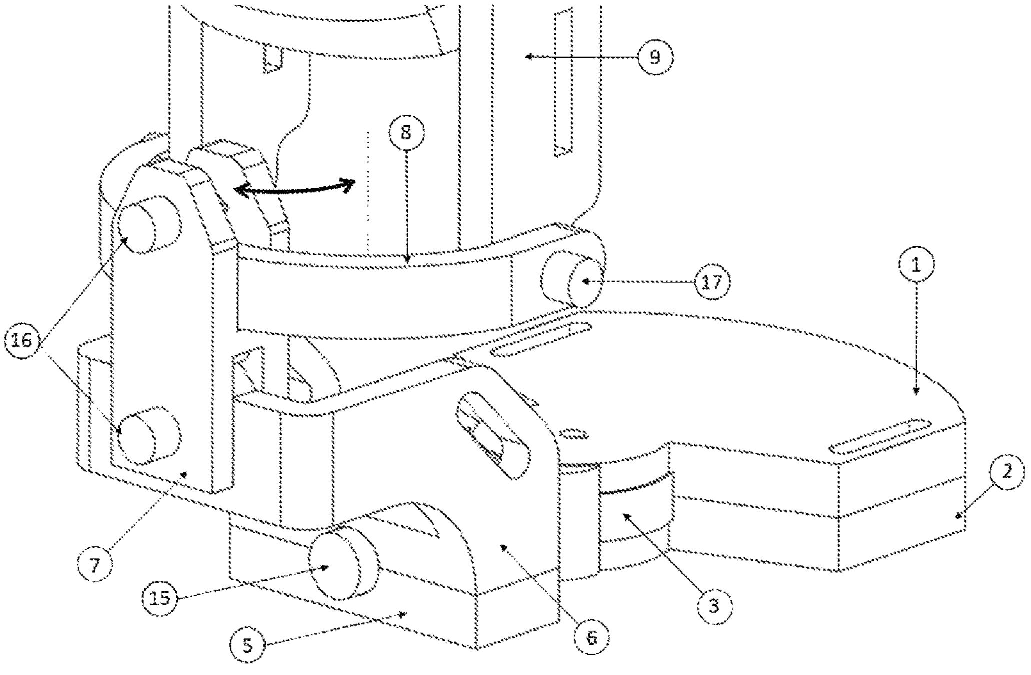
Figure 6C:
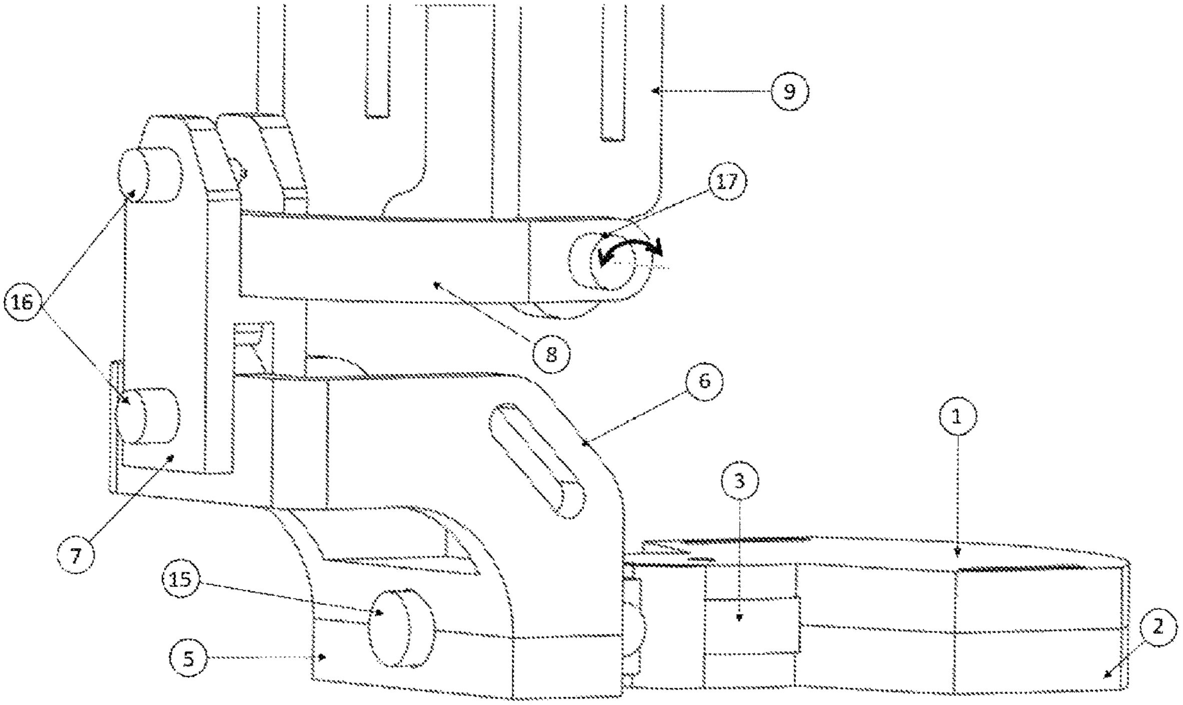

The three motions at the hind foot level give the corresponding response to these motions, which allows the hind foot to follow the forefoot, as shown in FIG. 6. The actuator A4 (16) provides the rolling motion as shown in FIG. 6(*a*) with a range of 70-degree inversion and 20-degree eversion. The actuator A4 (16) also provides the yawing motion of the hindfoot as shown in FIG. 6(*b*), a motion of 70-degree each in adduction as well as abduction. The pitching motion of the hind foot is carried out through the actuator A5 (17), with a range of 20-degree plantarflexion and 70-degree dorsiflexion, as indicated in FIG. 6(*c*).

Apart from the six corrective motions, the orthosis supports two other motions. The linear (sliding) motion in FIG. 7 includes sliding of the pair of slider links (11) in the pair of calf support links (9) with adjustment of a bolt (19) at desired locations. This motion helps the growth of the leg of the patient during the treatment. Using the revolute joint (FIG. 7), concerning the bolt (19), the pair of slider links (11) and the pair of thigh links (12) can be locked at any desired angle between zero to 90 degrees to allow for the folding and unfolding of the patient's leg along with his/her knee.

Figure 8A:
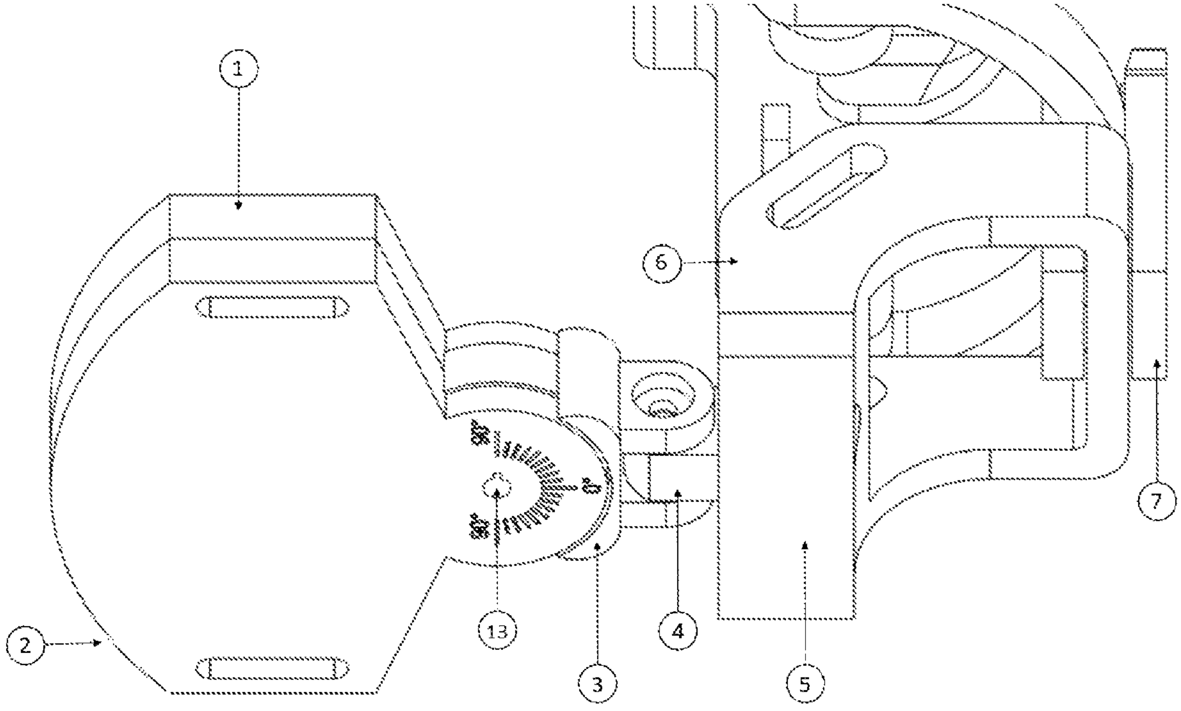
FIG. 8 shows: The locking and unlocking arrangements in the orthosis for corrective motions.
Figure 8B:
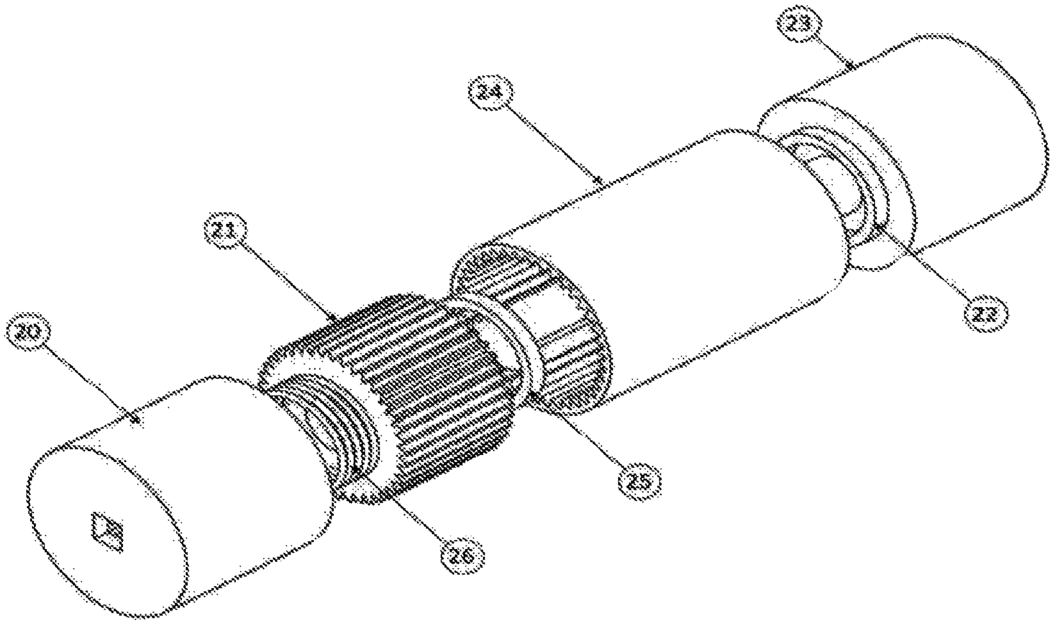

Step Motion Actuation & Locking/unlocking Mechanism: The lock and unlock provisions along with the dial gauges to the six corrective motion mechanisms permit the clinicians to manipulate and hold various parts of the foot for successive corrections. Out of the six motions shown in FIG. 5 and FIG. 6, a case of such arrangement is shown in FIG. 8 for the forefoot yawing (abduction/adduction) motion represented in FIG. 5(*a*). FIG. 8(*a*), shows the forefoot yawing (abduction/adduction) motion mechanism from a bottom view. The dial gauge has been provided around the cavity in the metatarsal bottom link (2) as shown in FIG. 4(*f*). To activate the forefoot yawing motion in a step of 5 degrees, and it's locking/unlocking, the actuator A1, assembly (13) with the dial gauge involves a closed loop controlled electro-magnetic actuation mechanism and with sensor as shown in the FIG. 8*b*).

For the six corrective motions, by the actuators A(1-5) (13-17), the orthosis relies on indexing a rotary motion to lock and unlock the orthosis using a plurality of splines created on an outer body (24), an inner slider (21) and an outer cap (20). In an initial position, the inner slider (21) rests midway between the outer cap (20) and the outer body (24) making the plurality of splines interlock the outer cap (20) and the outer body (24) connected to components that rotate relative to one another. Upon activation of an electromagnet (22), a permanent magnet (25) attached permanently to the inner slider (21) is repelled towards the outer cap (20) allowing for a rotation of the outer cap (20) facilitated by a motor (23). Once a predetermined amount of rotation is achieved, the electromagnet (22) is deactivated and a spring (26), attached to both the outer cap (20) and the inner slider (21) restores the inner slider (21) to the initial position of rest locking the orthosis in place until a further manipulation is required.

However, in case of a manual operation, a hex key can be inserted into a cavity in the outer cap (20) that pushes onto the inner slider (21) to cause the inner slider (21) to slide away from the outer cap (20) allowing for the predetermined amount of rotation. The inner slider (21) can then be restored to an original (e.g., initial) position as the spring (26) contracts to bring the inner slider (21) back to the original position of rest locking it in place once again when the hex key is removed.

All the locking/unlocking mechanisms are devised to restrict any involuntary tampering with the orthosis while carrying the patient. The dial gauges allow the paramedical/parents to perform necessary manipulations through remote guidance.

Figure 9:
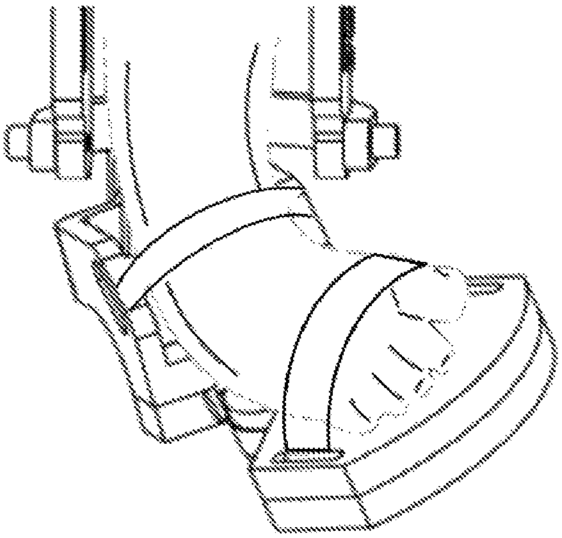
FIG. 9 shows: A severely deformed foot inside the developed corrective orthosis.

Orthosis to follow deformed foot: The orthosis, through its mechanism follows the deformed foot to the extreme positions. The orthosis is designed to tackle both "benign" (minimum deformity) and "severely deformed foot" (maximum deformity) as described using the Dimeglio Score system (e.g., 20-point classification system used to assess the severity of CTEV by evaluating the degree of deformity and reducibility). It implies that the orthosis can handle the most deformed foot, in which the deformities can be up to 90 degrees, as shown in FIG. 9.

The closed loop actuator along with a plurality of sensors also helps in data recording by the controller cum data acquisition (DAQ) system and hence deformity measurement and database creation before, during and after the treatment of the patient can be automated. This provision of online continuous measurement and recoding avoids the need of additional clubfoot (CTEV) deformity measurement before classifying it. The recorded data can be stored in a central database that paves the way for development of an expert system which can predict a more tailored, accurate and optimal treatment for patients.

An orthosis working for CTEV correction and maintenance: The orthosis allows the clinicians to correct the foot in the sequence as proposed in the Ponseti® Method (the manipulative casting method) i.e. simultaneous correction of deformities as per foot biomechanics. The orthosis permits, cavus correction by supinating the forefoot and adductus and varus deformities correction by the abduction of the forefoot with the lateral talus head as a fulcrum. After each manipulation, the orthosis is locked for 5 days to set the muscles. The graduated dial gauges permit the successive manipulations. With respect to the first stage of the Ponseti® Method (the manipulative casting method), the manipulations required for cavus correction are addressed using forefoot pitching and rolling. The adductus and varus correction is addressed using forefoot yawing and pitching. FIG. 10, shows the corrective orthosis motions being performed as per the Ponseti® Method (the manipulative casting method) in successive replication of the steps of casting.

Once the CTEV is corrected, the orthosis needs to be worn by the patient unilaterally similar to the maintenance orthosis prescribed in the Ponseti® Method (the manipulative casting method).

The orthosis also permits removal of residual equinus deformity at the ankle joint through an Achilles tenotomy, by the clinician, under local anesthesia, followed by locking the orthosis for 3 weeks. The orthosis has provision to provide 70 degree abduction and 15 degree dorsiflexion of complete foot similar to cast after the Achilles tenotomy.

The orthosis is designed to cater to various age ranges of the patient i.e. 2 weeks to 3 months, 3 months to 6 months, 6 months to 9 months, 9 months to 1 year and 1 year to 2 years, however it is preferred to start using the orthosis as a newborn.

Figure 1:
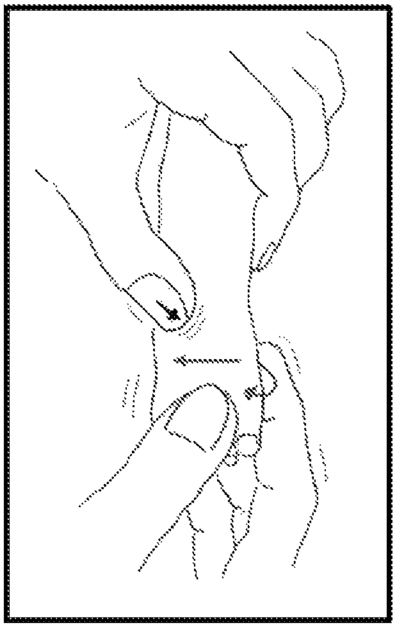
Figure 3A:
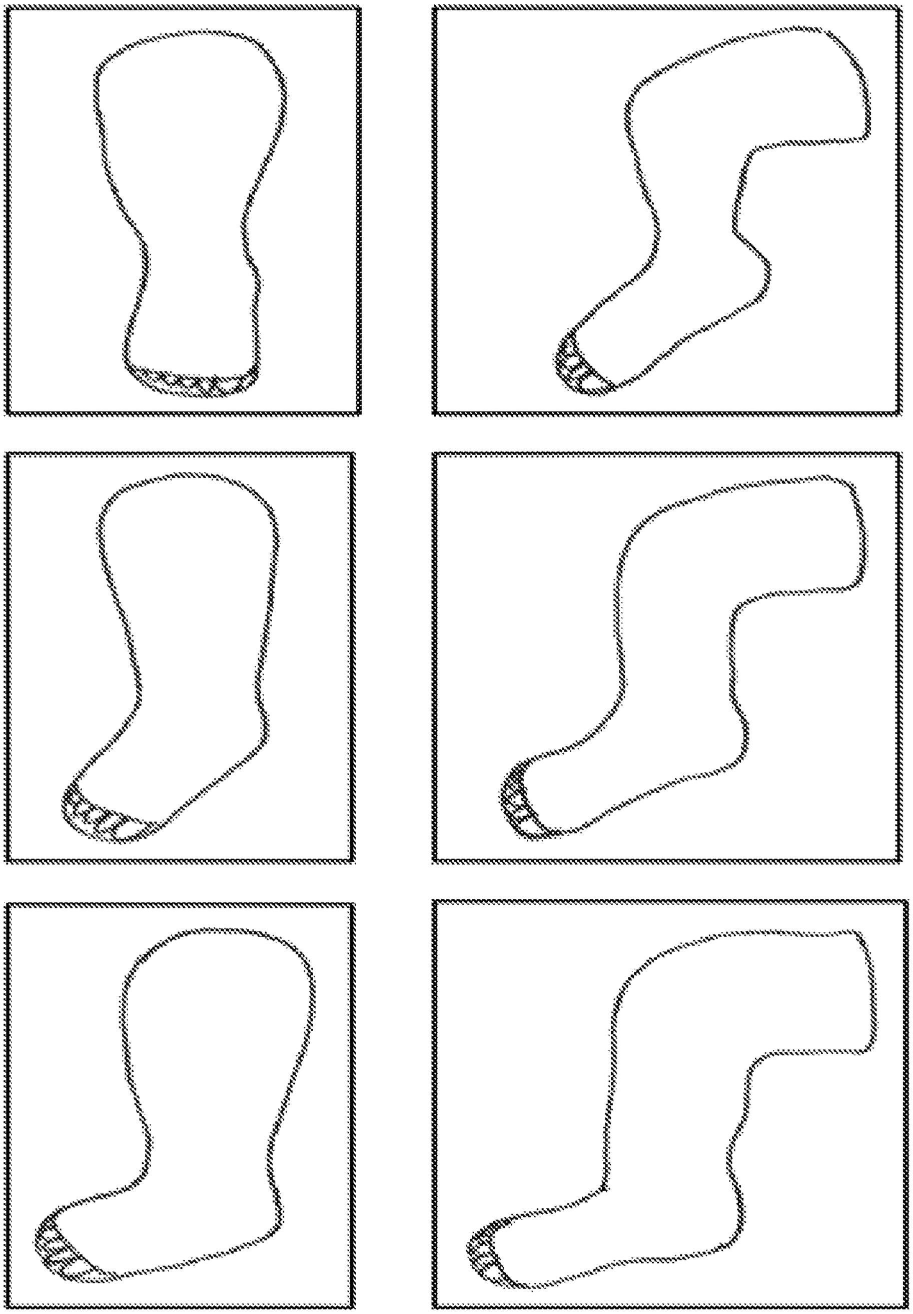
Figure 3B:
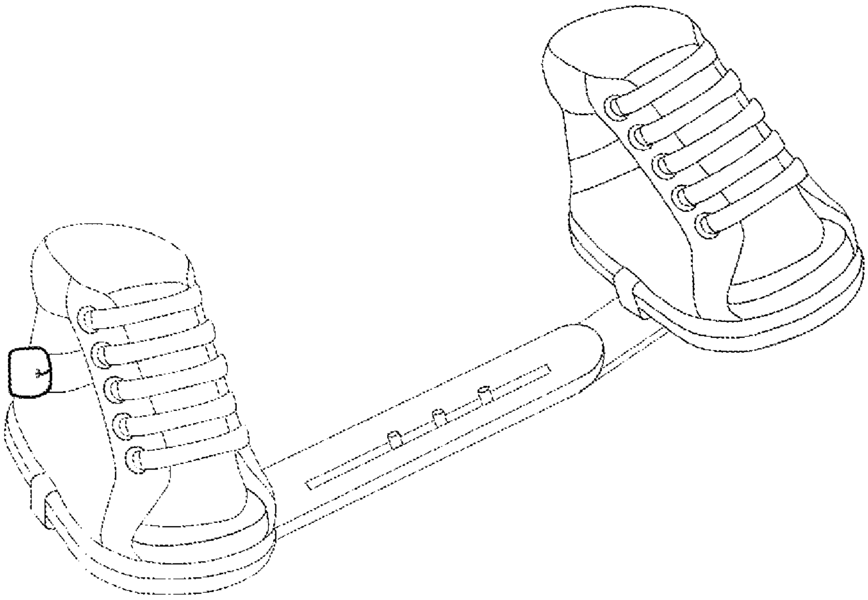
Figure 4A:
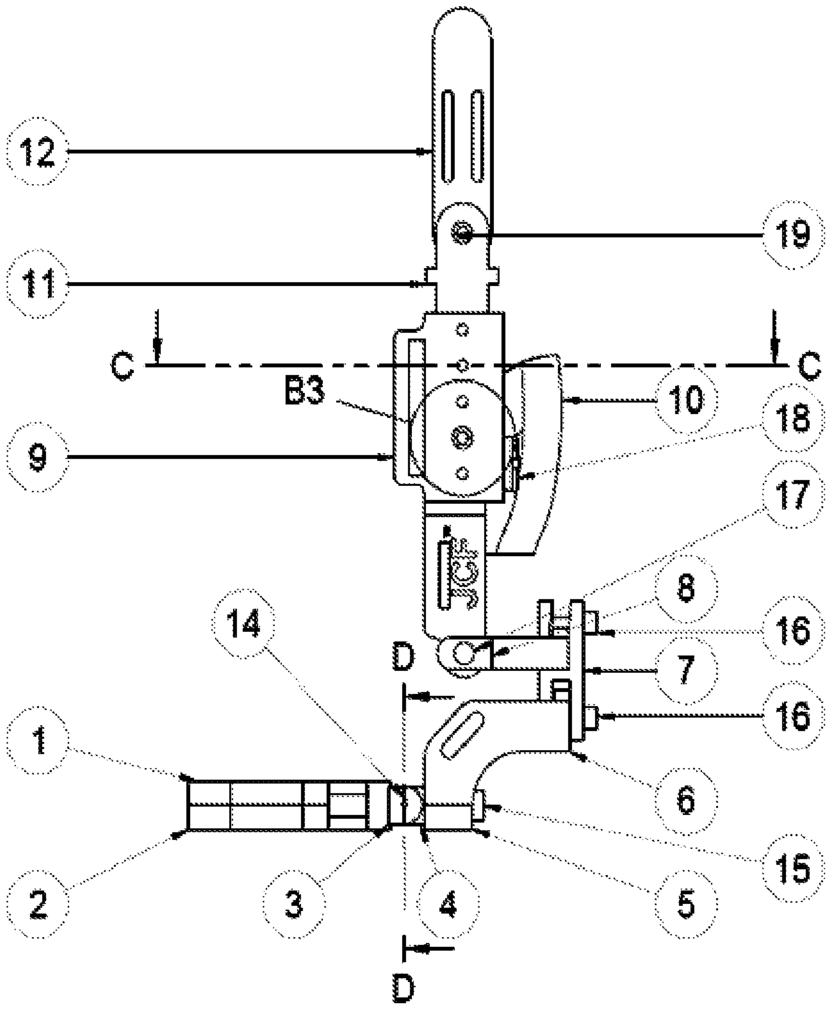
Figure 4B:
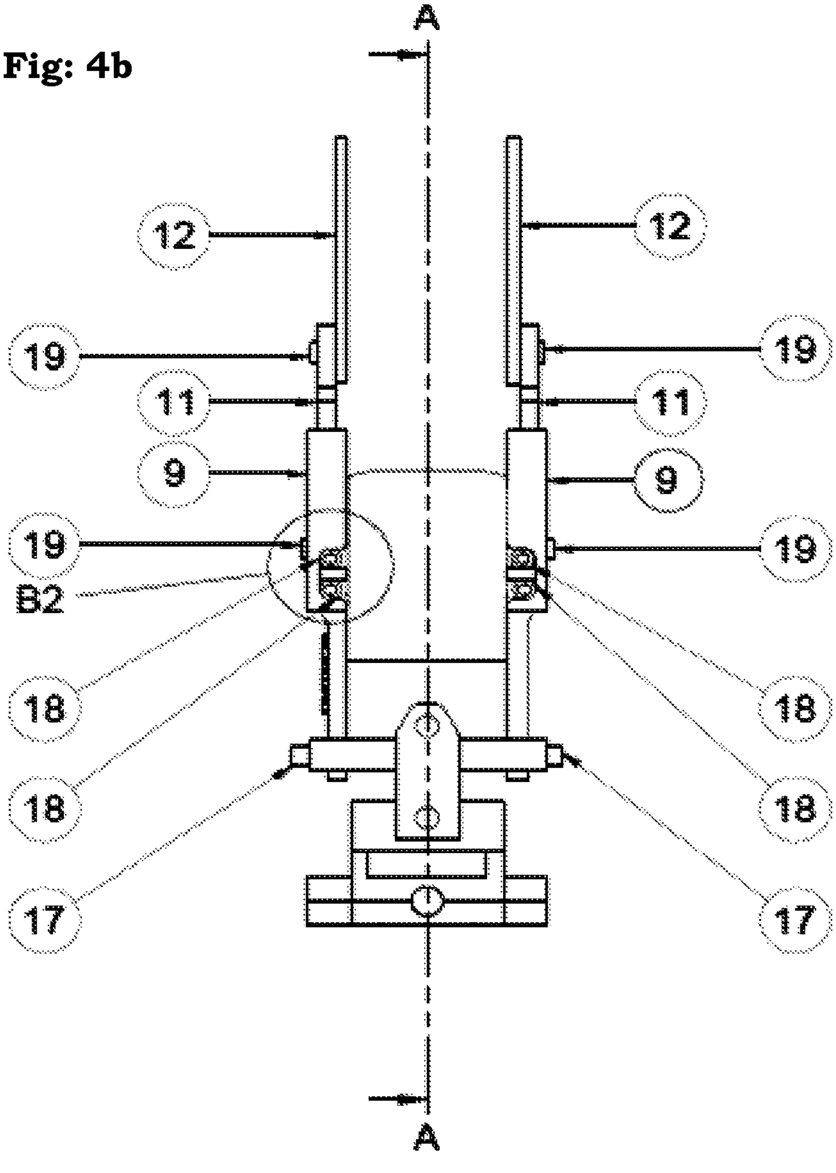
Figure 4C:
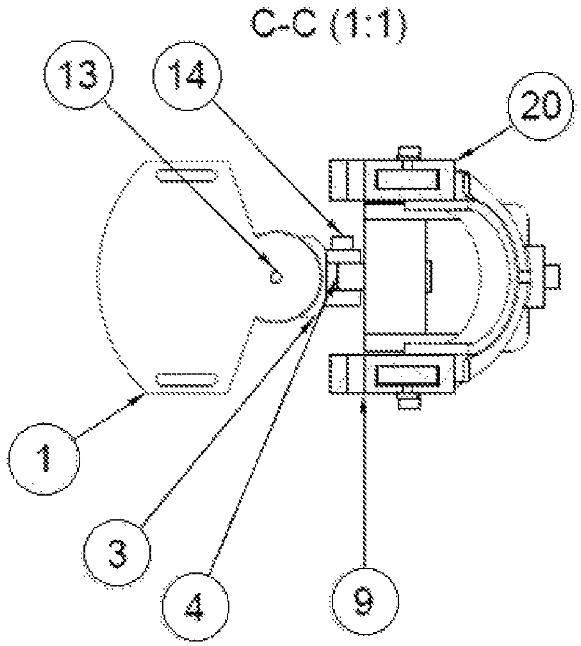
Figure 4D:
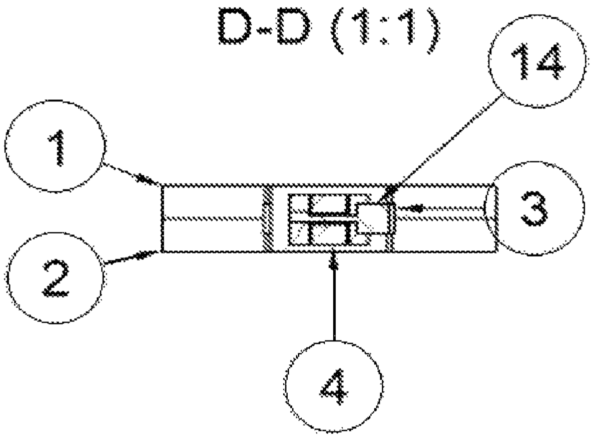
Figure 4E:
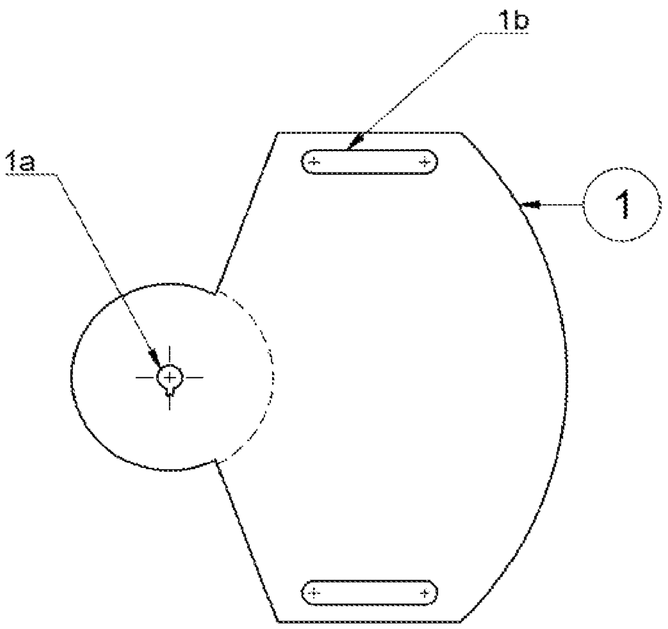
Figure 4F:
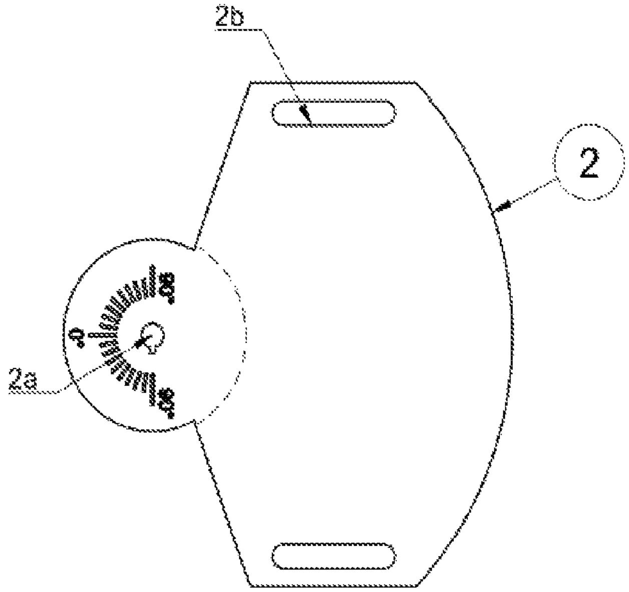
Figure 4G:
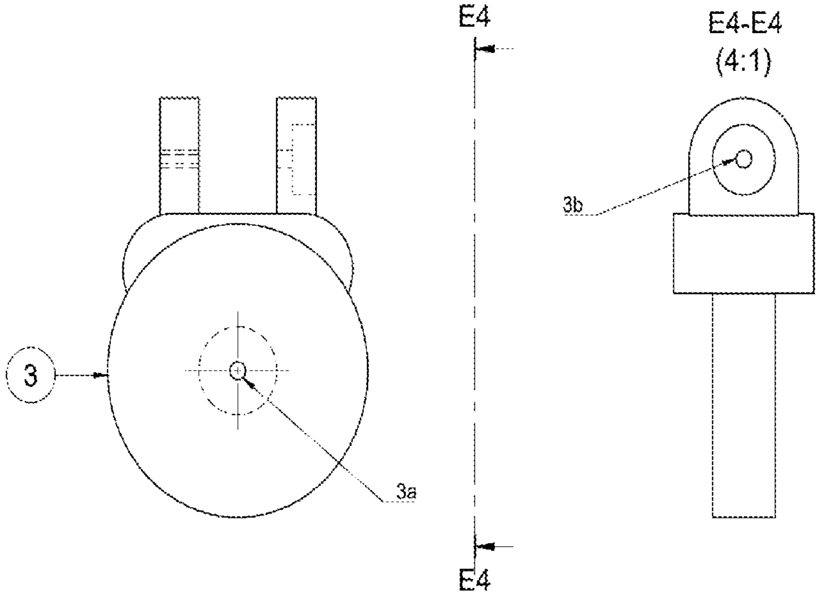
Figure 4H:
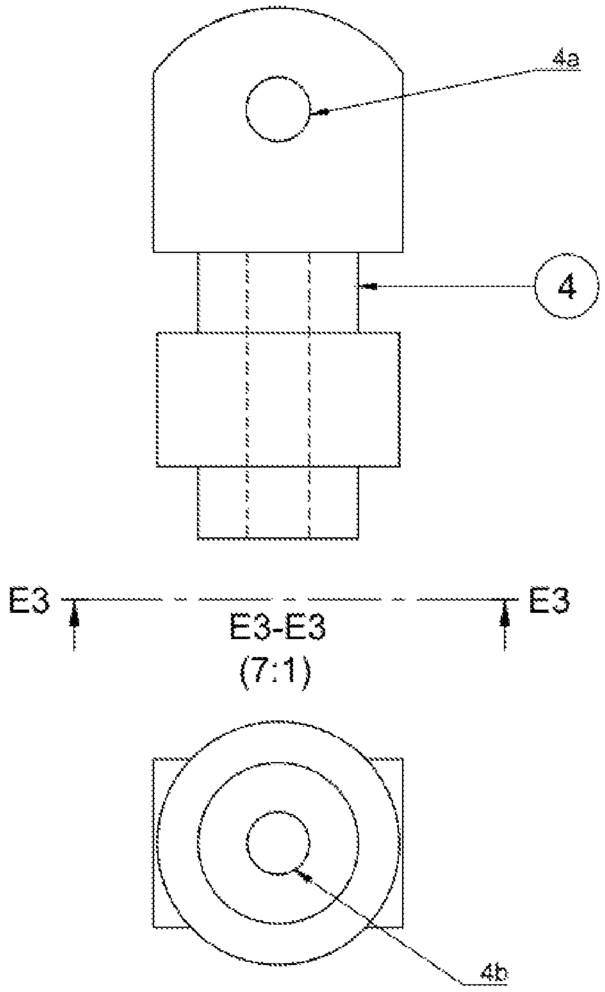
Figure 4I:
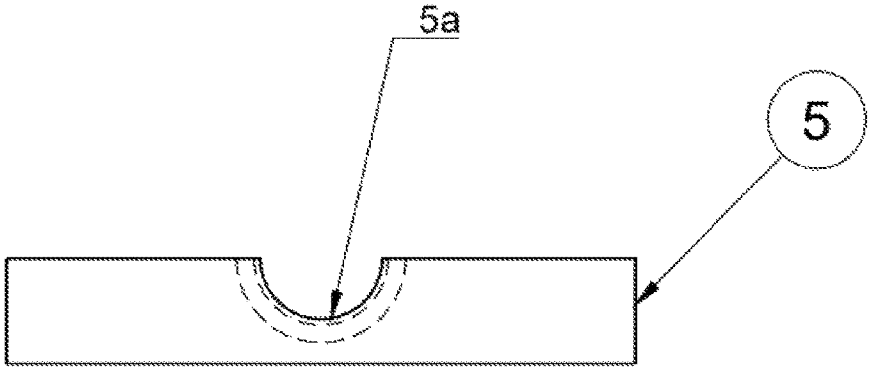
Figure 4J:
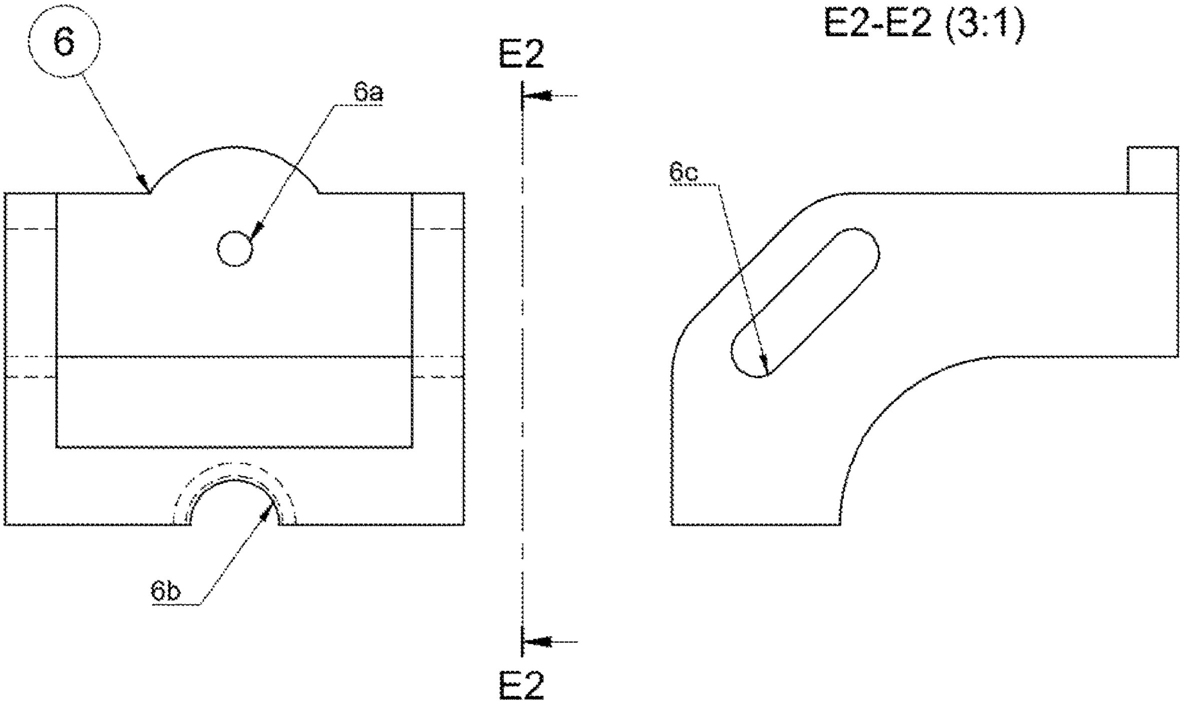
Figure 4K:
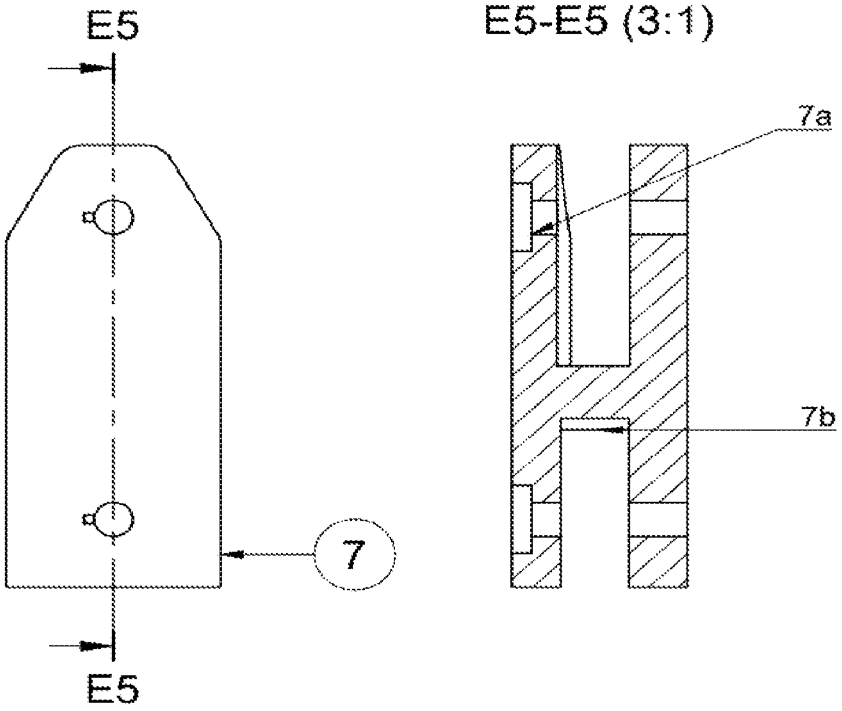
Figure 41:
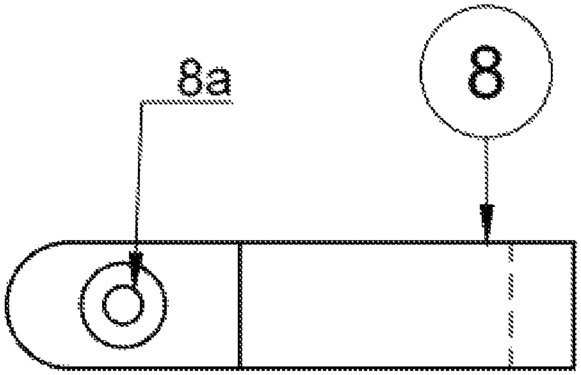
Figure 4M:
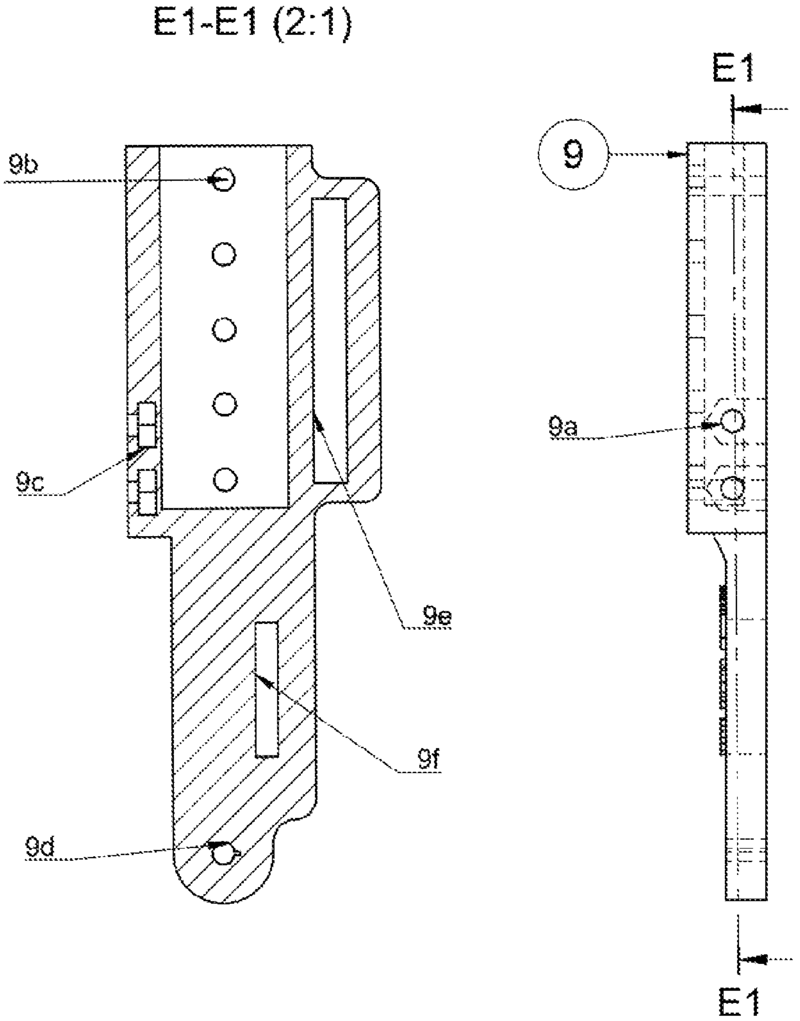
Figure 4N:
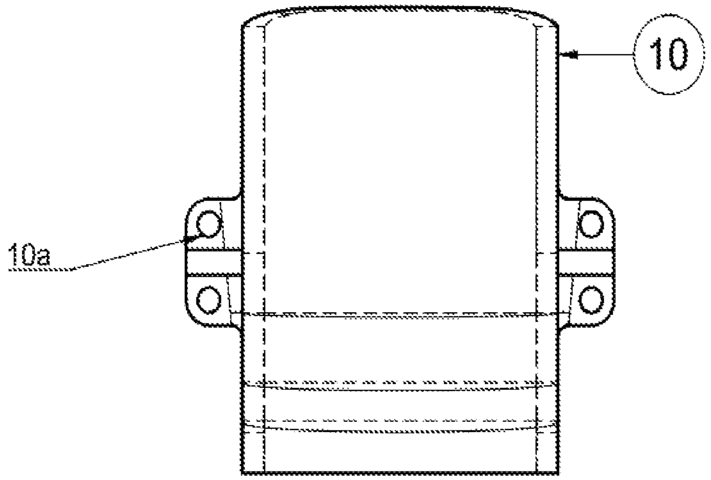
Figure 4O:
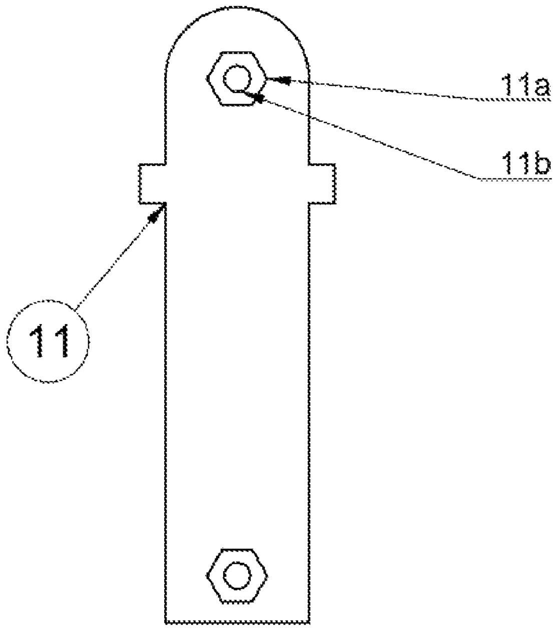
Figure 4P:
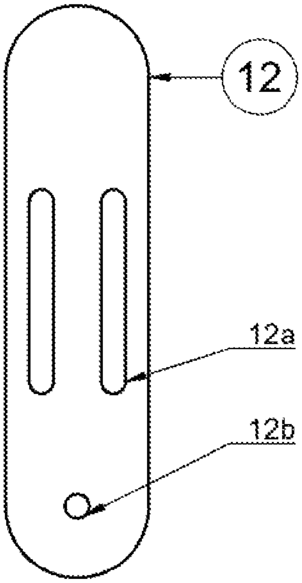

Design of the orthosis is parametric to customize it for the foot sizes of the patient. The orthosis also helps the clinician to identify the pivot point of talus head and lock the orthosis with respect to the pivot point for manipulation of the deformed foot for correction similar to FIG. 1.

Figure 7:
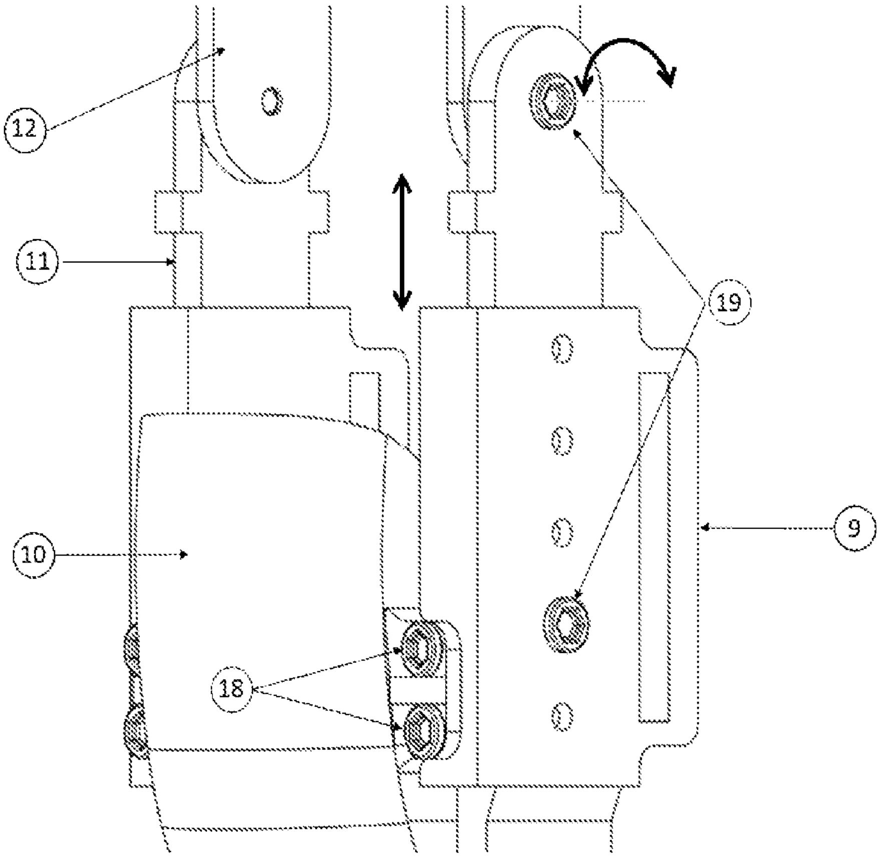
FIG. 7 shows: The sliding motion of the slider links and the rotation of the thigh links in the orthosis of the present invention.

The orthosis can be affixed to the patient's leg through calf and thigh supports, hence making it unilateral. When affixed, the motion at the knee replicates an above knee cast as shown in FIG. 7. The orthosis permits knee movement from fully straightened to completely bent (FIG. 7), without any discomfort to the patient.

Through the mechanism of this orthosis, it can also be used for maintaining the corrected position of the foot unilaterally as the patient grows, thereby avoiding the chance of relapse. It is much easier and stigma-free for parents and patients to use a unilateral orthosis as disclosed herein as compared to a bilateral orthosis of the prior art.

The orthosis can also be employed for relapse cases both for correction and maintenance. The maintenance involves keeping the foot at a 70 degree abduction, which can be easily obtained through a yawing motion of the forefoot. The orthosis is a unilateral device and looks like a high ankle shoe, thus avoiding the current stigma of bilateral FAB. The orthosis also supports foot manipulation by an informed parent and/or locally available paramedic under the remote guidance of the clinician, thereby minimizing patient travel to clinics, minimizing clinician time and encouraging treatment continuance.

As shown in FIG. 8, the corrective orthosis has a provision of a closed loop actuator along with a plurality of sensors for step motion as well as locking/unlocking mechanism. The orthosis can measure the CTEV deformity, initially for the assessment of the CTEV and later for quantifying the level of correction, every time the foot is manipulated with the help of integrated sensors.

Once the orthosis is mechanically established with direct operation by the clinicians and other trained medical professionals, it also supports remote foot manipulation by the clinician using closed loop actuators and a plurality of sensors for locking/unlocking on various joints. The remote foot manipulated can be caused by a controller that receives control signals from an IoT device operated by the clinician using a software application (FIG. 8). The sensors and actuators are placed along the lock and unlock provisions of the joint, along with dial gauges, which permits the autonomous manipulation of the orthosis for successive corrections using an algorithm based on Ponseti's understanding of foot biomechanics and level of deformity of the foot. The sensor and actuator operate under the instruction of a controller both guided and unguided through an intelligent algorithm.

The orthosis reduces the duration of overall treatment as the successive manipulations can be done after five days as the duration is sufficient for setting the muscles. The CTEV correction data can be stored in a database, thereby allowing for development of AI based algorithms/an intelligent system for CTEV correction. The orthosis paves the way for AI-based clubfoot assessment and treatment upon development and training of an algorithm by sufficient data sets in each category of clubfoot as stored in the database. The intelligent system can predict a more tailored, accurate, and optimal treatment for patients, hence enhancing the overall clubfoot (CTEV) management experience at all stakeholder levels including patients, patient parents, and clinicians.

Test Results

All the orthosis dimensions and motions are first verified by using the principles of science, followed by Computer Aided Design, Free Body Diagrams, Computer Aided Engineering and Proof of Concept (PoC) developed. Additively manufactured PoC, using polylactide (PLA) was submitted to clinicians for inputs and corrections in orthosis is done. A minimum viable prototype (MVP) manufactured using carbon fiber reinforced nylon was further tested for its functionality and inputs from the clinicians and parents. A fully functional orthosis of size zero i.e. two-week age was developed using additive manufacturing of a continuous as well as a chopped carbon fiber reinforced nylon polymer. The feedback and results are highly encouraging. The product has the success rate of that of the Ponseti® Method (the manipulative casting method) i.e. at least 90% with all the advantages over the conventional Ponseti® Method.

Advantageous Features of Orthosis:

- It is based on Ponseti's understanding of foot biomechanics.
- It incorporates eight motions namely, three corrective motions at a forefoot level, three corrective motions at a hind foot level, one motion to cater the growth of leg for the patient and one motion for knee flexibility of the patient.
- The lock and unlock provisions along with dial gauges to all the corrective motion mechanisms permit the clinicians to manipulate and hold various parts of the foot for successive corrections.
- The orthosis follows the deformed foot to the extreme positions.
- It allows the clinicians to correct the foot in the sequence as proposed in the Ponseti® Method (the manipulative casting method) i.e. simultaneous correction of all deformities, cavus correction by supinating the forefoot, adductus and varus deformities correction by the abduction of the forefoot with the lateral talus head as a fulcrum. After each manipulation, the orthosis is locked for 5 days to set the muscles. The graduated dial gauges permits the successive manipulations.
- It also permits removal of residual equinus deformity at an ankle joint through an Achilles tenotomy by the clinician under local anaesthesia, followed by locking the orthosis for 3 weeks.

It is designed to cater to various age ranges of the patient i.e. 2 weeks to 6 months, 6 months to 1 year and 1 year to 2 years, however it is preferred to start using the orthosis as a newborn.

The design of the orthosis is parametric to customize it for the foot sizes of the patient.

It helps the clinician to identify the pivot point of the talus head and lock the orthosis with respect to the pivot point for manipulation of the deformed foot for correction.

The orthosis can be affixed to the patient's leg through calf and thigh supports, hence rendering it unilateral.

It permits knee movement from fully straightened to completely bent.

Through the mechanism of this orthosis, it can also be used for maintaining the corrected position of the foot unilaterally as the patient grows, thereby avoiding the chance of relapse.

It can be used for relapse cases both for correction and maintenance.

It is a unilateral device and looks like a high ankle shoe, thus avoiding the current stigma of bilateral FAB.

It also supports foot manipulation by an informed parent and/or locally available paramedic under the remote guidance of the clinician, thereby minimizing patient travel to clinics, minimizing clinician time and encouraging treatment continuance.

It has provision of a closed loop actuator along with a plurality of sensors for step motion as well as locking/unlocking mechanism.

It can measure the CTEV deformity, initially for the assessment of the CTEV and later for quantifying the level of correction, every time the foot is manipulated with the help of integrated sensors.

It supports remote foot manipulation by the clinician using actuators and sensors on various joints along with a controller and IoT device connected to the terminal at the clinician facility, wherein the clinician remotely controls the orthosis using a software application.

It reduces the duration of overall treatment as the successive manipulations can be done after five days as the duration is sufficient for setting the muscles.

It is much easier and stigma-free for parents and patients to use a unilateral orthosis as described herein as compared to a bilateral orthosis of the prior art.

The CTEV correction data can be stored in a database, thereby allowing for development of AI based algorithms/an intelligent system for CTEV correction.

It paves the way for AI-based clubfoot assessment and treatment upon development and training of an algorithm by sufficient data sets in each category of clubfoot as stored in the database.

The developed intelligent system can predict a more tailored, accurate, and optimal treatment for patients.

Following are the Parts of the Orthosis:

| Reference Numerals | Part Name |
|---|---|
| {1} | Metatarsal Top |
| {2} | Metatarsal Bottom |
| {3} | Pitch & Yaw link |
| {4} | Forefoot Roll link |
| {5} | Hindfoot Lower Base |
| {6} | Hindfoot Top Base |
| {7} | Yaw Guide Base |
| {8} | Hindfoot Yaw Link |

-continued

| Reference Numerals | Part Name |
|---|---|
| {9} | Calf Support Link |
| {10} | Calf Muscle Support |
| {11} | Slider Link |
| {12} | Thigh Link |
| {13} | A1 (Assembly with dial gauge for forefoot yawing motion and its locking/unlocking) |
| {14} | A2 (Assembly with dial gauge for forefoot pitching motion and its locking/unlocking) |
| {15} | A3 (Assembly with dial gauge for forefoot rolling motion and its locking/unlocking) |
| {16} | A4 (Assembly with dial gauge for hindfoot yawing/rolling motion and its locking/unlocking) |
| {17} | A5 (Assembly with dial gauge for hindfoot pitching motion and its locking/unlocking) |
| {18} | Bolt |
| {19} | Slider Bolt |
| {20} | Outer Cap (splined internally) |
| {21} | Inner Slider (splined extrnally) |
| {22} | Electromagnet |
| {23} | Motor |
| {24} | Outer body (splined internally) |
| {25} | Permanent Magnet (attached permanently to inner slider) |
| {26} | Spring |
| {27} | Abduction (Yawing-in) |
| {28} | Dorsiflexion (Pitching-up) |
| {29} | Eversion (Rolling-CW from-Front) |
| {30} | Abduction (Yawing-out) |
| {31} | Plantarflexion (Pitching-down) |
| {32} | Inversion (Rolling-CCW from Front) |

PRIOR ART REFERENCES

1. Faraj A A, Howorth C A, Nevelos A B. The use of adjustable hinged orthosis in treating talipes equinovarus. *Foot and ankle surgery.* 2004; 10(2):57 {58.
2. Lugo-Villeda L I, Frisoli A, Bautista F C, et al. Non-invasive biomechanical device for the club-foot medical treatment: A robotic rehabilitation analysis. In: 2008 2nd IEEE RAS & EMBS International Conference on Biomedical Robotics and Biomechatronics; IEEE; 2008. p. 323-328.
3. Khas K S, Pandey P M, Ray A R. Development of an orthosis for simultaneous three dimensional correction of clubfoot deformity. *Clinical Biomechanics.* 2018; 51:67-75 and Patent application number, 1336/DEL/2012 titled "Orthosis for Simultaneous Three-Dimensional Correction of Club Foot"
4. Mohamaddan S, Fu C S, Rasit A H, et al. Development of adjustable foot corrective device for clubfoot treatment. *Pertanika Journal of Science & Technology.* 2017; 25:251-258.
5. Vishnu V A, et. al. Design and development of orthosis for clubfoot correction in infants an additive manufacturing approach. *Materials Today: Proceedings.* 2019.
6. Mali H S, et al. "Development of remedial orthosis for ctev (clubfoot) patient through five corrective motions" application No. 201811028509 [http://ipindiaservices-.gov.in/PatentSearch/PatentSearch//ViewApplicationStatus]; 2018 [Accessed 26 May 2020].

Each of the appended claims defines a separate invention, which for infringement purposes is recognized as including equivalents to the various elements or limitations specified in the claims. Depending on the context, all references below to the "invention" may in some cases refer to certain specific embodiments only. In other cases, it will be recognized that references to the "invention" will refer to subject matter recited in one or more, but not necessarily all, of the claims.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particulars claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogues to "at least one of A, B and C, etc." is used, in general such a construction is intended in the sense one having skill in the art would understand the convention (e.g., "a system having at least one of A, B and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

The above description does not provide specific details of manufacture or design of the various components. Those of skill in the art are familiar with such details, and unless departures from those techniques are set out, techniques, known, related art or later developed designs and materials should be employed. Those in the art are capable of choosing suitable manufacturing and design details.

The terminology used herein is for the purpose of describing particular embodiments only and is not intended to be limiting of the present disclosure. It will be appreciated that several of the above-disclosed and other features and functions, or alternatives thereof, may be combined into other systems or applications. Various presently unforeseen or unanticipated alternatives, modifications, variations, or improvements therein may subsequently be made by those skilled in the art without departing from the scope of the present disclosure as encompassed by the following claims.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. An orthosis configured for clubfoot (CTEV) correction and maintenance based on a manipulative casting method comprising, a metatarsal top link (1), a metatarsal bottom link (2) and a pitch and yaw link (3) connected together by an actuator A1 (13) with the pitch and yaw link (3) placed between the metatarsal top link (1) and the metatarsal bottom link (2), wherein the metatarsal top link (1) and the metatarsal bottom link (2) are each provided with a pair of strap slots (1*b*, 2*b*) allowing a passage of a forefoot strap through the pair of strap slots (1*b*, 2*b*) such that the forefoot strap is configured to hold a baby foot;

the pitch and yaw link (3) is connected to a forefoot roll link (4);

the forefoot roll link (4) is connected to a hind foot assembly comprising a hind foot bottom base (5) and a hind foot top base (6) configured to execute a rolling motion of a forefoot;

a yaw guide base (7) has a rotating joint with the hind foot top base (6) configured to provide a rolling motion of a hind foot through an actuator A4 (16);

the yaw guide base (7) slides on a hind foot yaw link (8) and is configured to provide a yawing motion of the hind foot through the actuator A4 (16);

the hind foot yaw link (8) is suspended on a pair of calf support links (9) on a first side and a second side of the hind foot yaw link (8);

a calf muscle support (10) attached to the pair of calf support links (9) and configured to support the calf muscle.

2. The orthosis as claimed in claim 1, wherein the metatarsal top link (1) is superimposed on the metatarsal bottom link (2), each of which is provided with one of the pair of strap slots (1*b* and 2*b*) and are configured to hold the baby foot, wherein the metatarsal top link (1) and the metatarsal bottom link (2) are coupled with the pitch and yaw link (3) and are configured to support a plurality of metatarsals and to perform a yawing motion of the forefoot buoyed by the actuator A1 (13) through a first hole (3*a*), in which the actuator A1 (13) passes through a plurality of holes including the first hole (1*a*, 2*a*, 3*a*).

3. The orthosis as claimed in claim 1, wherein the pitch and yaw link (3) is held in place and connected to the forefoot roll link (4) by an actuator A2 (14) passing through a keyhole on the pitch and yaw link (3) and a keyhole on the forefoot roll link (4).

4. The orthosis as claimed in claim 1, wherein the forefoot roll link (4) comprises a rotating joint with the pitch and yaw link (3) configured to cause a pitching motion of the forefoot through an actuator A2 (14), in which the hind foot top base (6) is secured with the hind foot bottom base (5) and the forefoot roll link (4) is joined with the hind foot bottom base (5) and the hind foot top base (6) and is configured to provide the rolling motion of the forefoot using an actuator A3 (15), wherein the hind foot top base (6), the hindfoot bottom base (5) and the forefoot roll link (4) are connected to each other via said actuator A3 (15).

5. The orthosis as claimed in claim 1, wherein the hind foot assembly encompasses the hind foot bottom base (5), the hind foot top base (6) and the yaw guide base (7), in which the hind foot top base (6) is configured to support a talus.

6. The orthosis as claimed in claim 1, wherein the hind foot yaw link (8) is suspended on the pair of calf support links (9) on the first side and the second side of the hind foot yaw link (8) by an actuator A5 (17) through a hole (8*a*) on the hind foot yaw link (8) and a hole (9*d*) on at least one of the pair of calf support links (9) and is configured to cause a pitching motion of the hind foot.

7. The orthosis as claimed in claim 1, wherein the calf muscle support (10) is fixed to the pair of calf support links (9) using a fastener including a bolt (18) passing through a plurality of holes (9*a* & 10*a*), and wherein the pair of calf support links (9) comprise a multitude of holes (9*b*) at different levels/heights to be locked with a slider link (11) using a slider bolt (19), in which the slider link (11) has a pair of embedded nuts and bolt holes (11*a*, 11*b*) and each of the pair of calf support links (9) has a plurality of slots (9*e*, 9*f*) to draw a plurality of calf straps therethrough that are configured to tie around a leg.

8. The orthosis as claimed in claim 1, wherein a pair of slider links (11) are attached to the pair of calf support links (9), the pair of calf support links (9) having a plurality of holes (9*b*), which allows the pair of slider links (11) to have a linear motion inside the pair of calf support links (9), wherein the linear motion is configured to compensate for a growth of a leg during a treatment.

9. The orthosis as claimed in claim 1, wherein the calf muscle support (10) comprises a protrusion on a right side of the calf muscle support (10) and a protrusion on a left side of the calf muscle support (10), wherein each protrusion comprises a plurality of holes (10*a*) therein.

10. The orthosis as claimed in claim 1, wherein the orthosis includes a pair of thigh links (12) configured to attach and ground the orthosis with a patient thigh using a plurality of thigh straps passing through a slot (12*a*), wherein the pair of thigh links (12) are connected with a pair of slider links (11) through a rotating joint, for which a fastener including a bolt (18) passes between two holes (11*a* and 12*b*).

11. The orthosis as claimed in claim 1 further comprising a thigh link (12) having a hole (12*b*) at which one side of a slider link (11) is attached to using a slider bolt (19), wherein the thigh link (12) further has a pair of slots (12*a*) for a plurality of thigh straps that are configured to be secured around a thigh and support the thigh even when a knee is bent.

12. The orthosis as claimed in claim 1, wherein the orthosis involves eight motions, the eight motions comprising the rolling motion of the forefoot, a yawing motion of the forefoot, a pitching motion of the forefoot, the rolling motion of the hind foot, the yawing motion of the hind foot, a pitching motion of the hind foot, a motion configured to cater to a leg growth of a patient, and a motion configured to cater to knee movement of the patient.

13. The orthosis as claimed in claim 1, wherein the orthosis relies on indexing a rotary motion to lock and unlock the orthosis using a plurality of splines created on an outer body (24), an inner slider (21) and an outer cap (20), in which the inner slider (21) in an initial position rests midway between the outer cap (20) and the outer body (24) making the plurality of splines interlock the outer cap (20) and the outer body (24), wherein upon activation of an electromagnet (22), a permanent magnet (25) attached permanently to the inner slider (21) is repelled towards the outer cap (20) allowing for a rotation of the outer cap (20) facilitated by a motor (23), wherein once a predetermined amount of rotation is achieved, the electromagnet (22) is deactivated and a spring (26), attached to both the outer cap (20) and the inner slider (21) restores the inner slider (21) to the initial position, locking the orthosis in place until a manipulation is required.

14. The orthosis as claimed in claim 1, further comprising a hex key inserted into a cavity in an outer cap (20) that pushes onto an inner slider (21) to cause the inner slider (21) to slide away from the outer cap (20) and then be restored to an original position as a spring (26) contracts to bring the inner slider (21) back to the original position and lock the inner slider (21) in place when the hex key is removed.

15. The orthosis as claimed in claim 1, wherein the orthosis has a provision of a closed loop actuator, comprising the actuator A1 (13), along with a plurality of sensors configured for step motion as well as a locking/unlocking mechanism comprising a dial gauge.

* * * * *